United States Patent [19]

Robbat, Jr.

[11] Patent Number: 5,970,804
[45] Date of Patent: Oct. 26, 1999

[54] METHODS AND APPARATUS FOR ANALYSIS OF COMPLEX MIXTURES

[75] Inventor: Albert Robbat, Jr., Andover, Mass.

[73] Assignee: Trustees of Tufts college, Medford, Mass.

[21] Appl. No.: 08/841,074

[22] Filed: Apr. 28, 1997

Related U.S. Application Data

[63] Continuation-in-part of application No. 08/639,183, Apr. 26, 1996, Pat. No. 5,668,373.

[51] Int. Cl.[6] .................................................. G01N 30/54
[52] U.S. Cl. .................. 73/863.12; 73/23.41; 73/864.84
[58] Field of Search ........................... 73/864.84, 863.12, 73/23.41, 23.42; 219/438

[56] References Cited

U.S. PATENT DOCUMENTS

| | | | |
|---|---|---|---|
| 2,826,180 | 3/1958 | Lupfer et al. | 73/863.12 X |
| 3,733,908 | 5/1973 | Linenberg | 73/863.12 |
| 4,128,008 | 12/1978 | Linenberg | 73/863.12 |
| 4,344,917 | 8/1982 | Schorno | 73/863.12 X |
| 4,376,391 | 3/1983 | Brunnee | 73/863.12 |
| 4,707,603 | 11/1987 | Miemelä et al. | 250/339 |
| 4,980,131 | 12/1990 | Meuzelaar et al. | 422/78 |
| 4,982,097 | 1/1991 | Slivon et al. | 250/282 X |
| 5,072,115 | 12/1991 | Zhou | 250/281 |
| 5,175,430 | 12/1992 | Enke et al. | 250/282 |
| 5,247,175 | 9/1993 | Schoen et al. | 250/281 |
| 5,285,064 | 2/1994 | Willoughby | 73/863.12 X |
| 5,400,665 | 3/1995 | Zhu et al. | 73/863.12 |
| 5,440,119 | 8/1995 | Labowsky | 250/282 |
| 5,453,613 | 9/1995 | Gray et al. | 250/281 |
| 5,475,612 | 12/1995 | Espinosa et al. | 364/500 |
| 5,481,476 | 1/1996 | Windig | 364/498 |
| 5,588,988 | 12/1996 | Gerstel et al. | 96/101 |

OTHER PUBLICATIONS

Abraham et al., "Data Comparison Study Between Field and Laboratory Detection of Polychlorinated Biphenyls and Polycyclic Aromatic Hydrocarbons at Superfund Sites," *Haz. Waste & Haz. Mat.*, 461–473 (1993) vol. 10, No. 4 month not given.

Bendl et al., "MS–UTIL: a program for interpretation and manipulation of mass spectra and chemical structures," *Comput. Methods Programs Biomed.* 46:23–28 (1995) month not given.

Lareau et al., "Peak Identification for Mass Spectroscopy," *Surface and Interface Analysis*, 17:38–42 (1991) month not given.

Robbat et al., "Evaluation of a Thermal Desorption Gas Chromatograph/Mass Spectrometer: On–Site Detection of Polychlorinated Biphenyls at a Hazardous Waste Site," *Analytical Chemistry* 358–364 vol. 64, No. 4 Feb. 15, 1992.

Robbat et al., "On–Site Detection of Polycyclic Aromatic Hydrocarbons in Contaminated Soils by Thermal Desorption Gas Chromatography/Mass Spectrometry," *Analytical Chemistry* 1477–1483 vol. 64, No. 13 Jul. 1, 1992.

Stauffer et al., "Probability–Based–Matching Algorithm with Forward Searching Capabilities for Matching Unknown Mass Spectra of Mixtures," *Anal. Chem.* 1056–1060 vol. 57, No. 6, May 1985.

Steiger et al., Automated peak interpretation in low–resolution SIMS spectra; a comparison of two algorithms, *Vacuum* 321–327 (1983) vol. 33, No. 6, month not given.

*Primary Examiner*—Thomas P. Noland
*Attorney, Agent, or Firm*—Fish & Richardson P.C.

[57] ABSTRACT

This invention provides methods and apparatus for determining the presence or absence of a specific constituent in a mixture. A thermal desorption unit includes a body providing a desorption chamber, a removable end cap for closing the chamber, a desorber heating system arranged to heat the desorption chamber, a gas inlet to the desorption chamber, and a gas outlet from the desorption chamber. A valve assembly can operate in a run mode to direct a carrier gas to the thermal desorption unit gas inlet, and couple the thermal desorption unit gas outlet to an inlet of a sample analysis instrument. The valve assembly also can operate in a flush mode to direct the carrier gas to the inlet of the gas analysis instrument, direct a flushing gas to the thermal desorption unit gas inlet, and couple the thermal desorption unit gas outlet to an exhaust.

35 Claims, 16 Drawing Sheets

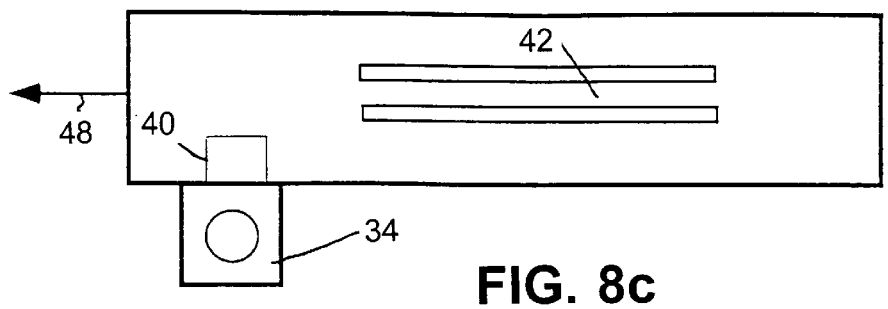
FIG. 8c
FIG. 8b
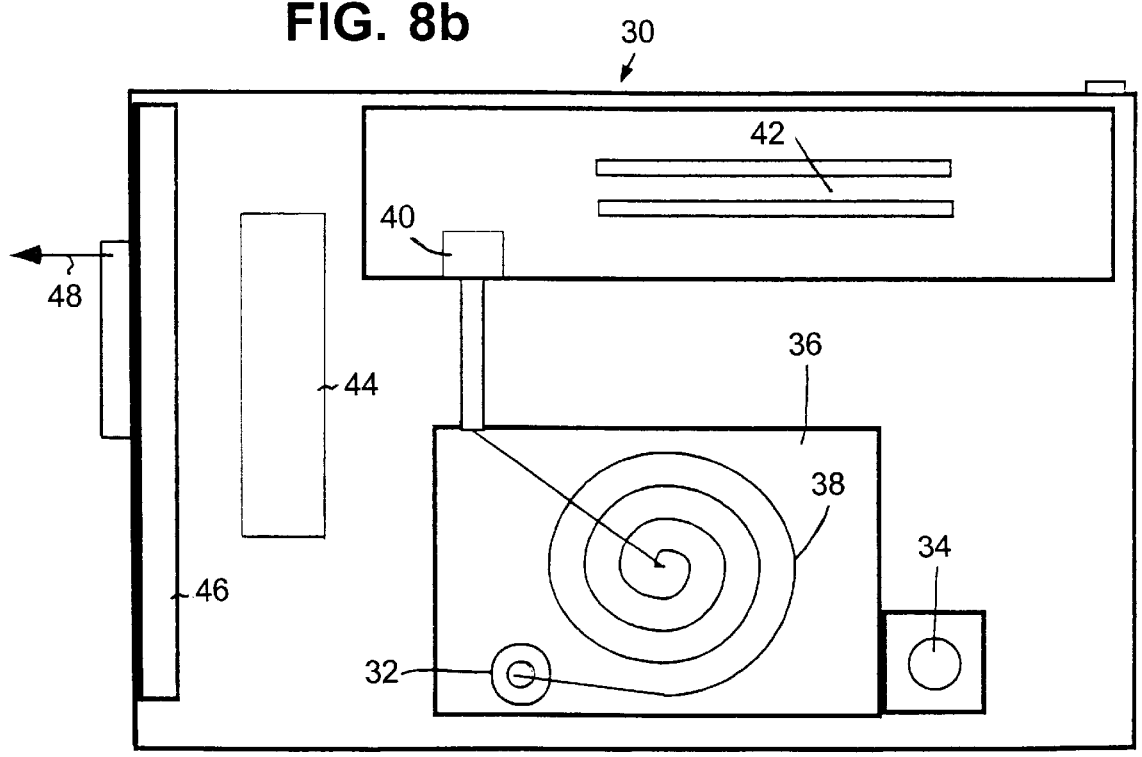

METHODS AND APPARATUS FOR ANALYSIS OF COMPLEX MIXTURES

CROSS-REFERENCE TO RELATED APPLICATION

This application is a continuation-in-part application of U.S. patent application Ser. No. 08/639,183, filed Apr. 26, 1996, by Albert Robbat, Jr. et al. and now U.S. Pat. No. 5,668,373.

BACKGROUND OF THE INVENTION

This invention relates to the rapid analysis of complex spectra produced by mixtures that contain multiple components that produce overlapping signal information.

The field of analytical chemistry involves the processes of sample collection, sample preparation, sample/constituent detection, data reduction, and statistics. For years method and instrument developers have made tradeoffs among the principal components that drive the analytical process, namely, the sample analysis rate, measurement sensitivity, and measurement precision and accuracy. To improve the overall sample analysis rates, much effort has been directed toward automation of the overall analytical process in an attempt to reduce the time of analysis and cost. Although automation has led to some improvements in precision and reductions in personnel costs, other attributes of the analytical process are much less affected, for example measurement sensitivity and accuracy.

Over the years, the term spectroscopy has come to mean the study (i.e., the identification, quantification, and theory) of electromagnetic radiation (including $\gamma$-ray, x-ray, ultraviolet/visible (UV/VIS), infrared (IR), microwave, electron spin, and nuclear magnetic resonance) as well as acoustic waves, electrons, and mass. In each of these spectroscopies, a source is used to probe specific regions within molecules or atoms.

For example, in atomic spectroscopy, flames, lasers, or plasmas, as well as other types of sources, are used to excite atom(s) that then absorb, emit, or fluoresce energy at characteristic wavelengths. This type of spectroscopy produces atomic species that produce narrow band peaks (called "lines") as opposed to molecular spectroscopy, e.g., UV/VIS or IR, which produces broad peaks ("bands") from molecules that have absorbed energy between 10 nm and 100 $\mu$m.

Mass spectrometry (MS) also employs a source to ionize molecules or atoms. Such sources include electron impact filaments, chemical ionization, or lasers, as well as other known sources. The gaseous ions are then separated by their mass-to-charge ratio (m/z) and detected as narrow band peaks. The output from a mass spectrometer is typically displayed as line signals.

In spectrometry, compounds or atoms are identified by their characteristic spectral peaks and their concentrations are determined from the corresponding peak intensities. For example, in mass spectrometry, an organic compound is ionized with the resulting gaseous fragment ions separated according to their differing masses and charges to form a characteristic "fingerprint." This fingerprint is compared to a set of patterns in a library and is identified on a best-fit probabilistic matched set basis, with a corresponding major ion current used to determine compound or atom concentration.

Mass spectrometry currently requires a separation step prior to analysis since simultaneous multiple compound detection results in many more fragment ions being produced than the probabilistic statistics can conventionally handle. Both gas and liquid chromatographies, as well as capillary electrophoresis separation, traditionally have been used prior to MS analysis for biological, chemical, environmental, petroleum, forensic, and many other types of analyses.

For example, thermal desorption gas chromatography/mass spectrometry (TDGC/MS) methods have recently been used to analyze nearly all U.S. Environmental Protection Agency (EPA) listed pollutant organics. The data from these methods have been accepted by both state and federal regulators and have supported numerous hazardous waste site investigations and cleanups. TDGC/MS methods can reduce the time of analysis (Robbat, Jr. et al., *Analytical Chemistry*, 64, 358–362, 1992; Robbat, Jr. et al., *Analytical Chemistry*, 64, 1477–1483, 1992; and Robbat et al., *Hazardous Waste and Hazardous Materials*, 10:461–473, 1993), but are limited in that they require a sample preparation step followed by gas chromatography separation of the individual constituents within the sample, and are restricted in the number of compounds they can analyze at one time.

Although standard laboratory instruments and methods provide good data quality, they do not meet the required sample throughput rates and trade measurement sensitivity for measurement precision and accuracy. To be cost-effective, current technologies do not provide compound-specification in "real" or "near real-time."

Various methods have been developed to improve and expedite the interpretation of mass spectra. For example, Gray et al., U.S. Pat. No. 5,453,613, describes a method of re-sorting mass spectra data files from chronological order to first ion-mass order and then to chronological order within separate ion-mass groupings. Local maxima are identified and then sorted and partitioned to obtain a set of deconvoluted spectra in which each element in the set is an identifiable compound. Compounds are then matched to reference spectra by conventional probabilistic matching routines.

Enke et al., U.S. Pat. No. 5,175,430, describes a time/separation spectral array detection system in conjunction with mass spectrometry to improve compound identification and decrease analysis time. Enke calls this time-compressed gas chromatography/mass spectrometry. Enke et al. note that the software approach of deconvolution has "not been significantly employed," because of the "insufficient quality and density in the data available." Enke et al solve this problem with a new apparatus (i.e., a hardware approach) that allows time-separation spectral detection to provide spectral data of high quality and density.

SUMMARY OF THE INVENTION

The invention features a new thermal desorber unit, that allows larger sample quantities, of gas, liquid, or solid, to be analyzed, e.g., by a mass spectrometer, and provides an overall system with advantageous accuracy, precision, and detection limits.

In another aspect, the invention is based on the discovery that by using a new method of spectral data analysis, specific constituents can be rapidly detected and quantified from conventional spectral data from a complex mixture of numerous constituents, all in one analysis run. The new data analysis method dispenses with or reduces the need for sample preparation and thus significantly decreases total analysis time and costs.

In one aspect, the invention features new thermal desorption units that include a chamber with a sample inlet, a sample outlet, a carrier gas inlet, and a carrier gas outlet, wherein the carrier gas inlet can serve as the sample inlet; a heater arranged to rapidly heat the chamber; a cooler, e.g., a cryogenic cooler, arranged to rapidly cool the chamber; conduits arranged to supply carrier gas to the chamber; a sample holder arranged inside the chamber so that carrier gas can carry a sample from the holder to the sample outlet; a controller arranged to actuate the heater and cooler at proper times; and a valve system arranged to control the flow of carrier gas to the chamber to carry a sample to the sample outlet.

The invention also features a method of desorbing a constituent from a sample, e.g., a non-volatile, semi-volatile, or volatile sample. This method includes the steps of dissolving the sample with a liquid, volatile solvent; heating the mixture to a low temperature at which the constituent remains a liquid and the solvent is vaporized; removing the solvent vapor from the liquid constituent; and heating the liquid constituent to a high temperature to vaporize the constituent, whereby the constituent is desorbed from the sample. In this method, the volatile solvent can have a boiling point lower than a boiling point of the constituent.

The invention further provides a method of isolating a constituent from a sample, e.g., a gaseous sample, using the thermal desorption unit described above. The method includes mixing the sample with a carrier gas to create a mixture, cooling the mixture to a first, low, temperature at which the constituent is liquified or solidified and the carrier gas remains a gas, removing the carrier gas from the constituent, and heating the constituent to a second, high, temperature to vaporize the constituent, whereby the constituent is isolated from the sample.

In other features of the invention, a gas phase sepation device can include the thermal desorption unit described above. Also, a gas phase detector can include the thermal desorption unit. The heater can include a cartridge heater, or a circuit that passes a current directly through a body of the chamber. The cooler may include a liquid nitrogen system, or a solid state cooling device.

In another aspect, the invention features a sample analysis system including a sample analysis instrument, a thermal desorption unit, and a valve assembly. The thermal desorption unit includes a body providing a desorption chamber, a removable end cap for closing the chamber, a desorber heating system arranged to heat the desorption chamber, a gas inlet to the desorption chamber, and a gas outlet from the desorption chamber. The valve assembly is structured and arranged to operate in a run mode to direct a flow of carrier gas to the thermal desorption unit gas inlet, and couple the thermal desorption unit gas outlet to an inlet of the sample analysis instrument. The valve assembly is also structured and arranged to operate in a flush mode to direct the flow of carrier gas to the inlet of the sample analysis instrument, direct a flow of flushing gas to the thermal desorption unit gas inlet, and couple the thermal desorption unit gas outlet to an exhaust.

The sample analysis system can include various additional features. The desorber heating system can include a circuit arranged to pass a current through the body to heat the body. The desorber heating system can alternatively include a cartridge heater or a circuit arranged to pass a current through the cartridge heater. The heating system can be structured and arranged to ballistically heat the desorption chamber from ambient temperature to a desorption temperature of at least about 300 or 325 degrees Celsius, e.g., in no more than about 6 to 16 seconds.

The thermal desorption unit can include a cooling assembly that is structured and arranged to cool the chamber to a cooled temperature that is substantially below ambient temperature. The cooling assembly can include a solid state cooling device.

The sample analysis instrument can include a gas phase separation device, such as a gas chromatograph. The sample analysis instrument may include a gas phase detector, such as a mass spectrometer, and which can have an inlet coupled to an outlet of the gas chromatograph column.

The desorption chamber can include a tube aligned approximately horizontally. e.g., within about 5 or 10 degrees of horizontal.

The thermal desorption unit can be structured and arranged to permit introducing a sample into the desorption chamber without opening the desorption chamber to atmosphere, as described herein.

The valve assembly can include a valve heating system adapted to controllably heat the valve assembly from ambient temperature to at least about 300 or 325 degrees Celsius.

The valve assembly can include a multi-port valve, a first port being coupled to a carrier gas supply, a second port being coupled to the thermal desorption unit gas inlet, a third port being coupled to the thermal desorption unit gas outlet, a fourth port being coupled to the sample analysis instrument inlet, a fifth port being coupled to a purge gas supply, and a sixth port being coupled to the exhaust. The valve heating system may be configured to heat the multi-port valve. The valve assembly may further include a flow controller, which includes a flow controller inlet coupled to the carrier gas supply, a first flow controller outlet coupled to the first port, and a second flow controller outlet connected to the fifth port, the flow controller being structured and arranged to selectively couple the flow controller inlet to any of the first flow controller outlet, the second flow controller outlet, and both the first and second flow controller outlets, wherein the carrier gas supply can also serve to flush the desorption chamber in the flush mode. The flow controller can be adapted to regulate the flow of carrier gas to the first port.

The invention also provides a method of isolating a constituent from a sample, e.g., a liquid sample, using the sample analysis system described above, wherein the sample includes the constituent and a solvent. The method includes first introducing the sample into the desorption chamber, then flushing the solvent out of the desorption chamber. Flushing includes operating the valve assembly in the flush mode to direct a flushing gas through the desorption chamber to the exhaust, whereby the constituent is adsorbed on a wall within the desorption chamber and the solvent is flushed out the exhaust; and desorbing the constituent by operating the valve assembly in the run mode to direct a carrier gas through the desorption chamber and into the analysis instrument, and heating the desorption chamber to a desorbing temperature while the carrier gas is flowing therethrough, thereby desorbing the constituent from the wall of the desorption chamber and carrying the constituent into the analysis instrument with the carrier gas.

Various additional features can be included in this method. For example, the desorption chamber can be heated by passing an electric current through the body of the chamber. Flushing can further include heating the desorption chamber to a flushing temperature that is lower than the desorbing temperature to flush out sample materials that are more vloatile than the constituent. Flushing can also include heating the valve assembly while flowing the flushing gas through the desorption chamber. Desorbing can include heating the valve assembly while operating in the run mode.

In another aspect, the invention features a method of isolating a constituent from a sample, e.g., a gaseous sample, that includes volatiles. The method includes cooling the desorption chamber to a condensing temperature below ambient temperature while operating the valve assembly in the flush mode to direct a flushing gas through the desorption chamber to exhaust; collecting the sample into the cooled desorption chamber while continuing to flush the chamber with flushing gas, thereby adsorbing the constituent onto a wall within the chamber; stopping sample collection; and desorbing the constituent by operating the valve assembly in the run mode to direct a carrier gas through the desorption chamber and into the analysis instrument, and heating the desorption chamber to a desorbing temperature that is above ambient temperature while the carrier gas is flowing therethrough, thereby desorbing the constituent from the wall within the desorption chamber and carrying the constituent into the sample analysis instrument with the carrier gas.

After adsorbing and before desorbing the constituent, the method can include the further step of flushing volatiles by heating the desorption chamber while in the flush mode to a flushing temperature that is lower than the desorbing temperature and sufficient to vaporize or at least remove volatiles from the sample. In one embodiment, the sample is collected while inhibiting oxygen from reaching the sample analysis instrument. The desorption chamber can be heated to the desorption temperature from ambient temperature within approximately 6 to 12 seconds or less. Desorbing can include carrying the desorbed constituent into a gas phase separator, and separating the constituent from other sample components desorbed from the chamber using the gas phase separator, e.g., a GC column.

In another aspect, the invention provides a method of isolating a constituent from a solid sample using the thermal desorption unit described above. The method includes placing the solid sample within the desorption chamber while the valve assembly is in the flush mode; sealing the desorption chamber from atmospheric air while continuing to operate in the flush mode; and desorbing the constituent by operating the valve assembly in the run mode to direct a carrier gas through the desorption chamber, and heating the desorption chamber to a desorbing temperature while the carrier gas is flowing therethrough, thereby desorbing the constituent from the solid sample and carrying the constituent to the inlet of the sample analysis instrument with the carrier gas.

The invention also provides a thermal desorption unit that includes an electrically conductive body providing a desorption chamber, a cap arranged to close the chamber, a gas inlet to the desorption chamber, a gas outlet from the desorption chamber, and a desorber heating system arranged to heat the desorption chamber, including a circuit arranged to pass a current through the body to resistively heat the body. The desorber heating system circuit can include a power supply, conductive wires connected between terminals of the power supply and the body, a temperature sensor being thermally coupled to the body, and a controller having a feedback circuit being coupled to an output of the sensor and controlling power output by the power supply based upon signals from the sensor.

In yet another aspect, the invention features a method for determining the presence or absence of a specific constituent in a mixture, e.g., a solid, liquid, or gas. The method includes the steps of: (a) applying energy to the mixture to cause constituents in the mixture to produce characteristic patterns of spectral lines and detecting quantity values at the spectral lines, wherein a quantity value may represent a contribution of two or more constituents; (b) comparing detected quantity values for a number N of spectral lines from a pattern of spectral lines characteristic of the specific constituent with known quantity values for the N spectral lines; (c) determining whether the detected quantity values for the N spectral lines fall within a predetermined error range, and; (d) determining the presence of the constituent in the mixture when detected quantity values of a number of spectral lines less than N fall within the predetermined error range.

The methods of the invention can be applied to mass spectrometry, in which case the spectral lines represent fragment ions of a constituent compound separated by a mass spectrometer, and the quantity value is abundance.

As used herein, a "constituent" is a compound, molecule, or element, that may or may not be part of a larger composition.

As used herein, a "spectral line" is a discrete value of a quantity value, e.g., wavelength, energy, mass, or mass/charge.

A "pattern" is a series of spectral lines, each in a precise position with respect to the others, that is unique and repeatable for a given molecule, compound, or atom. For example, in mass spectrometry, the pattern is based on the mass to charge ratio of ions that create the spectral lines. The position of the spectral lines is set by the mass-to-charge ratio, while the height of the lines (intensity) is determined by the abundance of ions at a particular m/z.

The invention further features another method for determining the presence or absence of a specific constituent in a mixture. In this method, the steps include: (a) applying energy to the mixture to cause constituents in the mixture to produce characteristic patterns of spectral lines and detecting quantity values at the spectral lines, wherein a quantity value may represent a contribution of two or more constituents; (b) calculating a set of relationships, e.g., ratios, $R_N$ of detected quantity values for a number N of spectral lines within a pattern characteristic of the specific constituent; (c) comparing relationships $R_N$ with a known set of relationships for the N spectral lines of the constituent in a library, wherein correspondence of the relationships $R_N$ to the known library relationships within a predetermined error range is taken to indicate that the constituent is present in the mixture; wherein if the relationships $R_N$ do not correspond to the known library relationships within the error range, (d)(i) selecting a first subset $N_S$ of N spectral lines wherein $N_S$ is less than N; (d)(ii) calculating a set of relationships $R_S$ of detected quantity values for the $N_S$ spectral lines in the first subset; (d)(iii) comparing the first subset relationships to the library relationships and recording a first subset variation value based on variations between the first subset relationships and the library relationships; (d)(iv) repeating the selecting, calculating, and comparing steps (i–iii) for different subsets $N_S$ of N spectral lines, and recording a variation value for each subset; and (d)(v) determining if a subset has a variation value within a predetermined error range and if so, using the subset to indicate that the specific constituent is present in the mixture.

Step (d)(v) of this method can be achieved by determining the subset with the minimum variation values, wherein a minimum variation value within the predetermined error range is taken to indicate that the specific constituent is present in the mixture. In step (c), the constituent can be indicated to be present in the mixture if sets of relationships, e.g., ratios, of less than N spectral lines correspond to the known library relationships within a predetermined error range, or the constituent can be indicated to be present in the mixture if sets of relationships of less than N but greater than N/2 spectral lines correspond to the known library relationships within a predetermined error range.

The method can include as a further step determining the concentration of the constituent in the mixture, by selecting a spectral line having the highest quantity value of the N spectral lines used to indicate the presence of the constituent, and using the quantity value as an indication of the concentration of the constituent in the mixture.

Alternatively, if a spectral line having the highest quantity value of the N spectral lines does not form a subset having a variation value within a predetermined error range, the concentration can be determined by taking a spectral line having the second highest quantity value of the N spectral lines, and using the second highest quantity value as an indication of the concentration of the constituent in the mixture.

As another alternative, if a spectral line having the highest quantity value of the N spectral lines does not form a subset having a first variation value within a predetermined error range, and other of the N spectral lines form subsets having a variation value within a predetermined error range, correcting said highest quantity value based on said first variation value to provide a corrected quantity value, and using the corrected quantity value as an indication of the concentration of the constituent in the mixture.

In another embodiment, for a given peak in total ion current produced by a mixture input to a mass spectrometer through a separation unit, the analysis can be repeated at one or more different points in the peak and used to determine that the constituent is present in the mixture only if more than one of the analyses, e.g., at least 2 or 3 out of 4 different analyses, indicates the presence of the constituent.

The method can include, prior to the comparison step (c), a step of subtracting a background value from each detected spectral line quantity value. The methods also can include the steps of passing the mixture through a separation unit before entering a mass spectrometer, the constituent eluting from the column characteristically within a predetermined time range, and the analysis steps (b) through (d) are performed substantially only at times in which the constituent characteristically elutes from the column.

The methods can be carried out without prior sample clean-up, whereby the mixture is introduced into a mass spectrometer by the technique of programmed thermal desorption. Or, the methods can be carried out without prior separation, whereby the mixture is introduced into a mass spectrometer by the technique of programmed thermal desorption.

In another aspect, the invention features an apparatus for determining the presence or absence of a specific constituent in a mixture including (a) an energy source arranged to apply energy to the mixture to cause constituents in the mixture to absorb, emit, or fluoresce particles of energy; (b) a spectral separation unit arranged to separate the particles of energy into patterns of spectral lines, wherein each line represents one particle, the size of each line represents the quantity of each type of particle, and each pattern of spectral lines is characteristic for one constituent, and wherein a quantity value may represent a contribution of two or more constituents; (c) a detector arranged to detect the particles and produce data representing the patterns of spectral lines; (d) a memory arranged to store the data, a library containing a known set of ratios for spectral lines of a pattern characteristic of the constituent, and predetermined error ranges; and (e) a processor arranged to analyze the data, wherein the processor is programmed to carry out the methods described herein.

As another embodiment, the invention features a computer program for analyzing data representing patterns of spectral lines of a constituent in a mixture, wherein each line represents one particle from the constituent, the size of each line represents the quantity of each type of particle in the mixture, and each pattern of spectral lines is characteristic for one constituent, the program residing on a computer-readable medium and including instructions for causing a processor to carry out the steps described above.

The invention also features a spectrometer, e.g., a mass spectrometer, including the computer program.

The new method provides an easily implemented, yet powerful and rapid approach to analyzing spectra of complex mixtures for identifying individual constituents or groups of constituents even when the spectra of some of the constituents overlap. The new method enables the operator to use any instrument that produces spectral line data and to analyze that data quickly by analyzing all of the compounds in a sample in one analysis run. The new method provides substantial improvements in accuracy, precision, and sensitivity without the need for (1) extensive sample cleanup (or fractionation), e.g., solid phase and liquid extraction, and/or gel permeation or column chromatography to extract the targeted compounds from sample contaminants; or (2) pre-analysis separation, e.g., gas chromatography, to separate individual target compounds from each other, prior to analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 8b is a schematic diagram of a thermal desorption gas chromatograph/mass spectrometer including the TD of FIG. 8a.

FIG. 8c is a schematic diagram of a thermal desorption/mass spectrometer including the TD of FIG. 8a connected directly to the mass spectrometer.

DETAILED DESCRIPTION

The new thermal desorber units (TD) allow large sample quantities, both liquid and solid, to be analyzed, e.g., by a mass spectrometer or any other gas phase detector, and thus provide an overall system with desirable accuracy, precision, sensitivity, and throughput. The valving for the TD is arranged to inhibit contaminants that can be damaging to a gas chromatography column from ever entering the column. In addition, the TD can be heated by passing a current through it, improving the speed with which the TD's temperature can be raised.

The invention also features a new method of data analysis that enables specific constituents to be rapidly identified and quantified in one analysis run of a complex mixture of numerous constituents. The invention can be implemented in hardware or software, or a combination of both. The data analysis method can be implemented in computer programs executing on programmable computers each comprising a processor, a data storage system (including memory and/or storage elements), at least one input device, such as a mass spectrometer, and at least one output device, such as a CRT or printer. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Spectral Analysis System

Data Analysis Method

There are two aspects of spectral measurements. The first is identification of constituents in a sample, and the second is determination of the concentration at which the detected constituents are present in the sample. Both of these aspects are carried out by the data analysis method.

Constituent Identification

Figure 1:
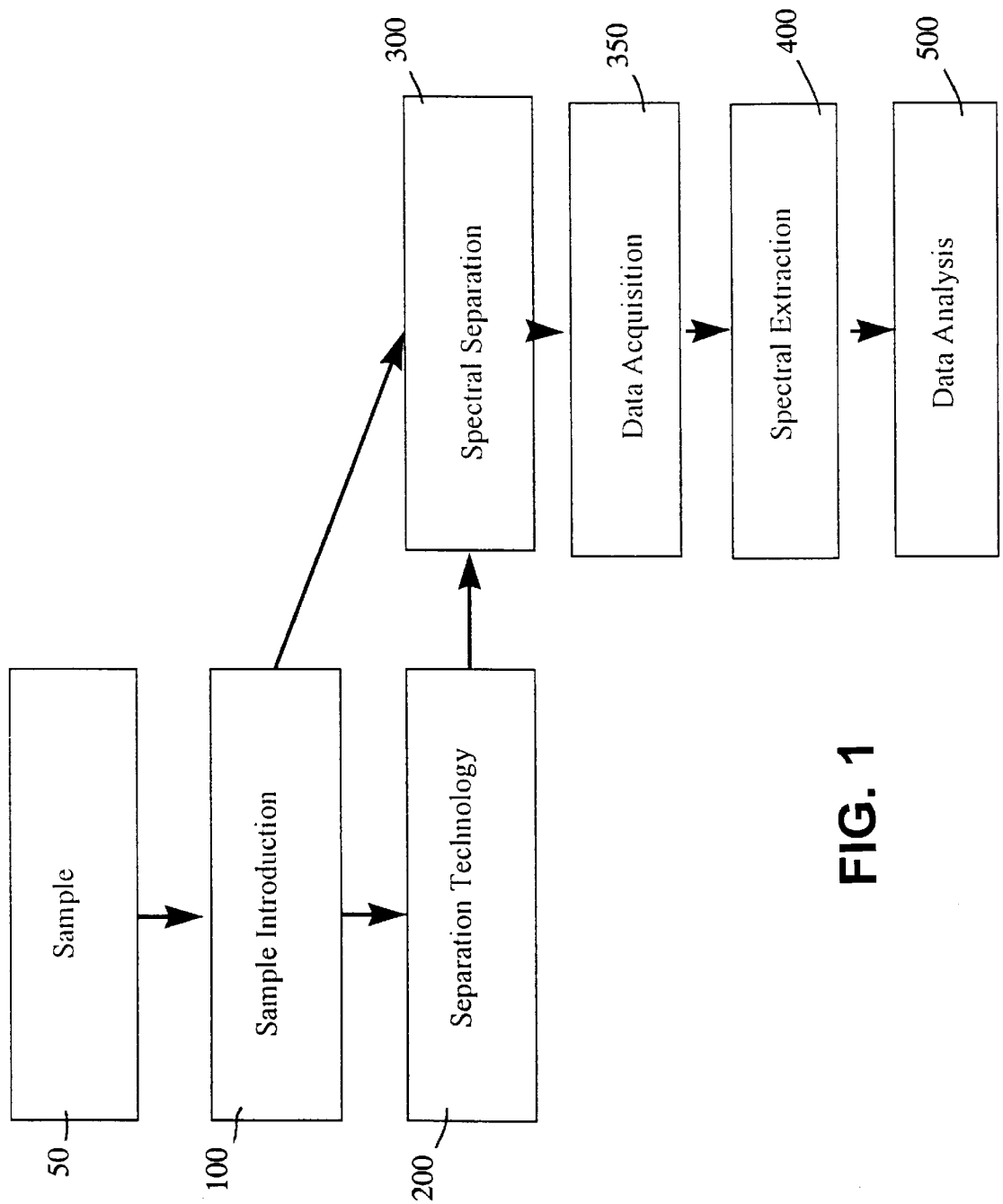
FIG. 1 is a flow chart providing a general overview of the method of spectral analysis.

As shown in FIG. 1, the method includes several steps, or modules including several steps. Some of these steps are carried out manually or mechanically by a device, and others are carried out by a programmed computer. Samples, e.g., from a solid, gaseous, or liquid, complex mixture are collected by conventional methods (step 50) and introduced into the analytical device (step 100).

Although not required for the method, separation step 200 improves overall quality of analysis. Any separation technology can be used, for example, gas or liquid chromatography, or other devices that separate molecules or constituents present in complex mixtures. The time it takes for a molecule or compound to travel through a chromatographic separation device is called the "retention time." The thermal desorption (TD) technology described herein enables the direct injection of constituents from solid, liquid, or gaseous materials without the need for separation step 200.

Spectral separation, step 300, is a required step of the data analysis method, but can be carried out by a wide variety of known spectrometers as described herein. Data Acquisition module 350 is based on standard software that instructs the spectral analysis device to obtain the raw data produced by the spectral separation step (300) (see, e.g., the three-dimensional data shown in FIG. 7), and to store that data in an unprocessed data file or buffer in memory. This raw data is then processed by the Spectral Extraction (400) and Data Analysis (500) modules of the data analysis method.

In general, the Data Analysis module 500 includes Background Correction steps, 501 (see FIG. 4), to correct for instrument noise or background (discussed below), and a number of specific method steps that compare ratios of quantity values of the detected spectral lines representing each constituent in the complex mixture with a library of known ratios representing all constituents to be detected. The library is stored in a computer memory and is tailored to contain information relevant to the constituents to be analyzed by a particular device. For example the library can include environmental sample data, biochemical sample data, or pharmaceutical sample data. Libraries can also be created for atomic emission data and essentially any type of quantity values that characterize organic or inorganic compounds.

Figure 13:
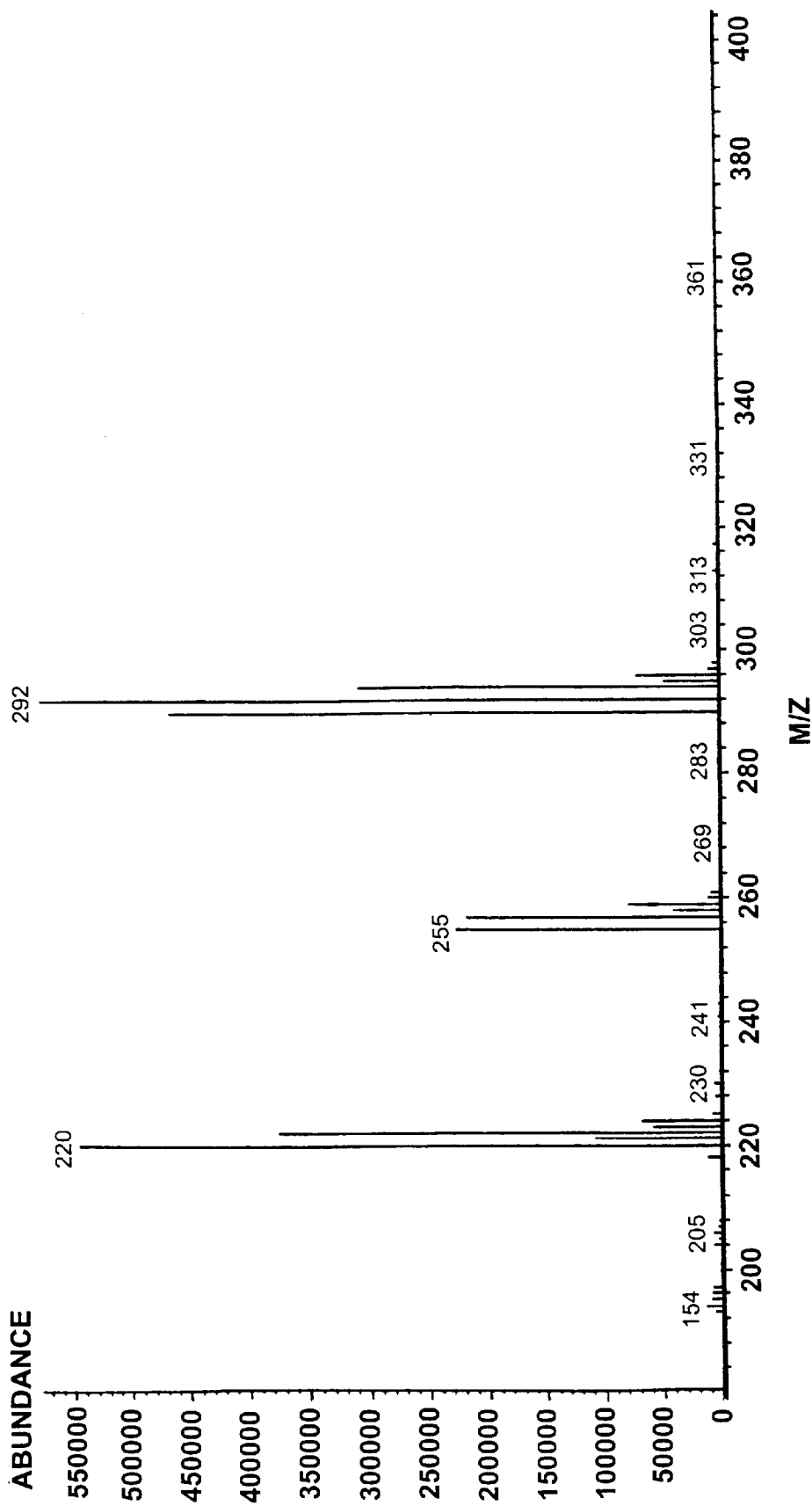
FIG. 13 is a MS spectrum of a clean standard solution of 2,2',4,6-tetrachlorobiphenyl.

To establish a library, the operator prepares a clean sample for a spectral analysis of each constituent to be analyzed (see, e.g., FIG. 13), and selects the particular spectral line to be used as the "main spectral line," and several "common spectral lines," e.g., the "main ion" and "common ion" in MS analysis, to represent that constituent (for example, in FIG. 13, the fragment ion at 292 m/z would be the "main ion," and fragment ions 220 and 256 would be the "common ions.").

The total number N of representative spectral lines (main plus common spectral lines) is selected by the operator depending on the total number of spectral lines that the constituent expresses, the number of strong lines, the number of unique lines, etc. For example, a constituent may have 10 total spectral lines. However, some of those spectral lines may be very small in terms of their relative abundance. Thus, the operator ignores those small lines and selects a number N that is smaller than the total number of spectral lines, e.g., 5 rather than 10.

As discussed herein, a number of spectral lines "less than N" is used to determine the presence of a given constituent to accommodate possible interfering spectral lines from other constituents or contaminants in a mixture, e.g. lipids and PCBs. Thus, N is selected, in part, based on the smallest "number less than N" of spectral lines, which is typically three if there are two or more constituents in a sample mixture (or if there are only two compounds present, but their spectral line patterns are very different). This provides the minimum of two spectral line pair relationships, e.g., ratios, required to unambiguously identify a constituent in a complex mixture. Thus N is typically at least four.

In the interests of computational efficiency, N is selected based on having as few spectral lines as possible, and of those, as many large (abundant) spectral lines as possible that are different from lines in other constituents that may be present in the mixture. Thus, if there are several constituents in a mixture that are known to have overlapping spectral lines, the operator may choose a somewhat larger N to ensure that one of the constituents is not improperly counted as a different constituent.

There can be up to 100 common spectral lines per constituent, whereas only one main spectral line is selected (thus a maximum N is 101). However, in practice in MS analysis of many organic compounds, there will be three to five, often three, common spectral lines that, together with the main spectral line, suffice to unambiguously identify a constituent or compound. Generally, the operator would use the same rationale to select the appropriate number of spectral lines in other types of spectral analysis.

The main spectral line is selected based on uniqueness and quantity value, e.g., abundance in MS analysis. Thus, the operator selects the spectral line that is preferably as unique as possible and that has a quantity value as high as possible for a particular constituent. The quantity value of this main spectral line is used to determine the quantity or concentration of a constituent in a sample. Thus, the quantity value is an important selection factor, because the spectral line having the highest quantity value will be less affected by the signal-to-noise (S/N) ratio of the device. However, the spectral line having the highest quantity value is not selected if it is found in numerous other constituents. In those cases, a spectral line that is more unique, but has a lower quantity value should be selected as the main spectral line.

The common spectral lines are used for constituent identification and for quantification in some specific instances as described below.

Once the main and common spectral lines are selected, the operator determines or accesses a set of ratios of the quantity values of the selected spectral lines. The set of ratios is unique for each of the constituents to be detected and is based on known quantity values for each of the selected spectral lines of the constituent to be detected. The sets of quantity value ratios for the selected spectral lines of the constituents of interest are stored in the library. The ratios can be based simply on the quantity values (e.g., A/B, where A represents the quantity value of a first spectral line, and B represents the quantity value of a second spectral line), but also can be based on other mathematical functions of this ratio, e.g., the logarithm of A/B, the sin of A/B, and the square root of A/B. The specific mathematical function used does not matter, as long as the differences in the quantity values of the spectral lines in a set can be used to uniquely characterize a specific constituent.

For example, to establish the library of ratios to analyze mass spectrometry data, the operator selects a main ion to represent a particular constituent (typically the most abundant ion for that constituent), and sets its abundance value (intensity) to 100%. Next, the operator selects the common ions and sets their values to lower intensity values according to their known abundance values compared to the abundance of the main ion. The intensity values for use in mass spectrometry are based on the known fragment ion patterns and corresponding intensity data of all constituents to be identified, e.g., from the over 90,000 organic compounds listed in the National Institute of Standard and Testing library (NIST, Gaithersburg, Md.). Other known collections of compound information are available (e.g., Wiley AccessPack™, Palisade Corp., Newfield, N.Y.). Ratios are determined for other pairs of fragment ions for the constituent to create a set of ratios that uniquely represents that constituent.

Such sets of ratios are recorded for each constituent to be detected in later unknown samples. The sets of ratios for all constituents to be detected are incorporated into the data analysis software in the form of a "library," or look-up table.

For example, Table 1 below, for use in mass spectral analysis, is the "library" showing mass/charge (m/z) values, which provides position information in a mass spectrum, and relative abundances (in parentheses) of selected fragment ions of forty different organic chemicals including polychlorinated biphenyls (PCBs), polycyclic aromatic hydrocarbons (PAHs), organochlorine pesticides, and an internal standard. For these compounds, Table 1 provides information for one main ion, and typically three common ions, that together can be used to unambiguously identify a particular compound. The relative intensity (abundance) between the ions is established by setting the main ion to 100%, and setting the intensity of the common ions accordingly.

For example, the first row in Table 1 shows the compound naphthalene, and the mass/charge (m/z) for four fragment ions representing that compound, 128, 129, 127, and 102. Table 1 also shows the relative abundances in parentheses (100%, 11%, 10%, and 7%). In the simple case where there are no co-eluting constituents that have the same spectral line or lines, if naphthalene is detected in a sample, each of the relative intensities, one against the other, of the detected compound naphthalene will be in the same ratios shown in Table 1. A complicated, and more typical case is where there are a 1000 or more fragment ions present in an unknown sample, that overlap each other to varying degrees, and make a comparison of the four fragment ions that represent naphthalene very difficult without the new data analysis method.

TABLE 1

Compound-specific MS Fragment Ions and Percent Relative Abundance

| Organics | m/z (%) | m/z (%) | m/z (%) | m/z (%) |
|---|---|---|---|---|
| naphthalene | 128(100) | 129(11) | 127(10) | 102(7) |
| acenaphthylene | 152(100) | 151(22) | 150(14) | 153(14) |
| acenaphthene | 154(100) | 153(87) | 152(48) | 151(14) |
| fluorene | 166(100) | 165(87) | 167(15) | 163(12) |
| phenanthrene | 178(100) | 176(15) | 179(15) | 177(8) |
| anthracene | 178(100) | 176(15) | 179(15) | 177(8) |
| fluoranthene | 202(100) | 203(20) | 200(16) | 201(11) |
| pyrene | 202(100) | 203(20) | 200(16) | 201(11) |
| benzo[a]anthracene | 228(100) | 226(22) | 229(20) | 227(7) |
| chrysene | 228(100) | 226(22) | 229(20) | 227(7) |
| benzo[b]fluoranthene and benzo[k]fluoranthene | 252(100) | 250(34) | 253(25) | 251(13) |
| benzo[a]pyrene | 252(100) | 250(34) | 253(25) | 251(13) |
| dibenz(a,h)anthracene | 278(100) | 279(23) | | |
| Indeno(1,2,3-cd)pyrene | 276(100) | 277(24) | 274(18) | 275(12) |
| benzo(g,h,i)pyrene | 276(100) | 277(24) | 274(18) | 275(12) |
| Cl-1 | 188(100) | 190(34) | 152(31) | 189(0) |
| Cl-2 | 222(100) | 224(70) | 226(11) | 223(0) |
| Cl-3 | 256(100) | 258(100) | 260(34) | 257(0) |
| Cl-4 | 292(100) | 290(81) | 294(60) | 291(0) |
| Cl-5 | 326(100) | 328(70) | 324(65) | 325(0) |
| Cl-6 | 360(100) | 362(92) | 358(52) | 359(0) |
| Cl-7 | 394(100) | 396(100) | 392(45) | 395(0) |
| Cl-8 | 430(100) | 428(88) | 432(65) | 429(0) |
| Cl-9 | 464(100) | 462(75) | 466(72) | 463(0) |
| Cl-10 | 498(100) | 500(92) | 496(78) | 497(0) |
| BHC | 219(75) | 181(100) | 221(39) | 263(0) |
| Heptachlor | 100(100) | 274(52) | 272(65) | 261(0) |
| Aldrin | 263(100) | 261(65) | 101(100) | 293(42) |
| Heptachlor epoxide | 353(100) | 355(81) | 351(52) | 357(39) |
| Endosulfan 1 | 195(100) | 241(87) | 207(75) | 387(0) |
| Dieldrin | 108(100) | 263(20) | 277(15) | 207(0) |
| 4,4'-DDE | 246(100) | 318(81) | 316(60) | 235(0) |
| Endosulfan 2 | 195(100) | 241(87) | 207(75) | 387(0) |
| 4,4'-DDD | 235(100) | 237(65) | 165(45) | 178(11) |
| Endosulfan sulfate | 272(100) | 274(93) | 277(45) | 195(0) |
| 4,4'-DDT | 246(20) | 235(100) | 237(70) | 178(0) |
| Endrin | 317(56) | 315(39) | 345(25) | 343(19) |
| Endrin aldehyde | 345(45) | 347(25) | 343(29) | 349(10) |
| Endrin ketone | 317(52) | 319(34) | 315(36) | 321(11) |
| Pyrene-d10 | 212(100) | 211(56) | 210(31) | |

The Spectral Extraction module 400 and Data Analysis module 500 can be started once: (1) the ratios for the quantity values of the selected spectral lines of each of the compounds to be detected are established in a library, (2) other system parameters such as minimum signal value, retention index (if used), quantity value thresholds, and various error ranges, as well as integration interval and general information on the compound (constituent) as described below are established in a parameter library, (3) a sample is introduced into the spectrometer (step 100), (4) a characteristic spectral fingerprint is produced (spectral separation step 300), and (5) the data is stored in a computer memory (Data Acquisition Step 350).

Figure 2:
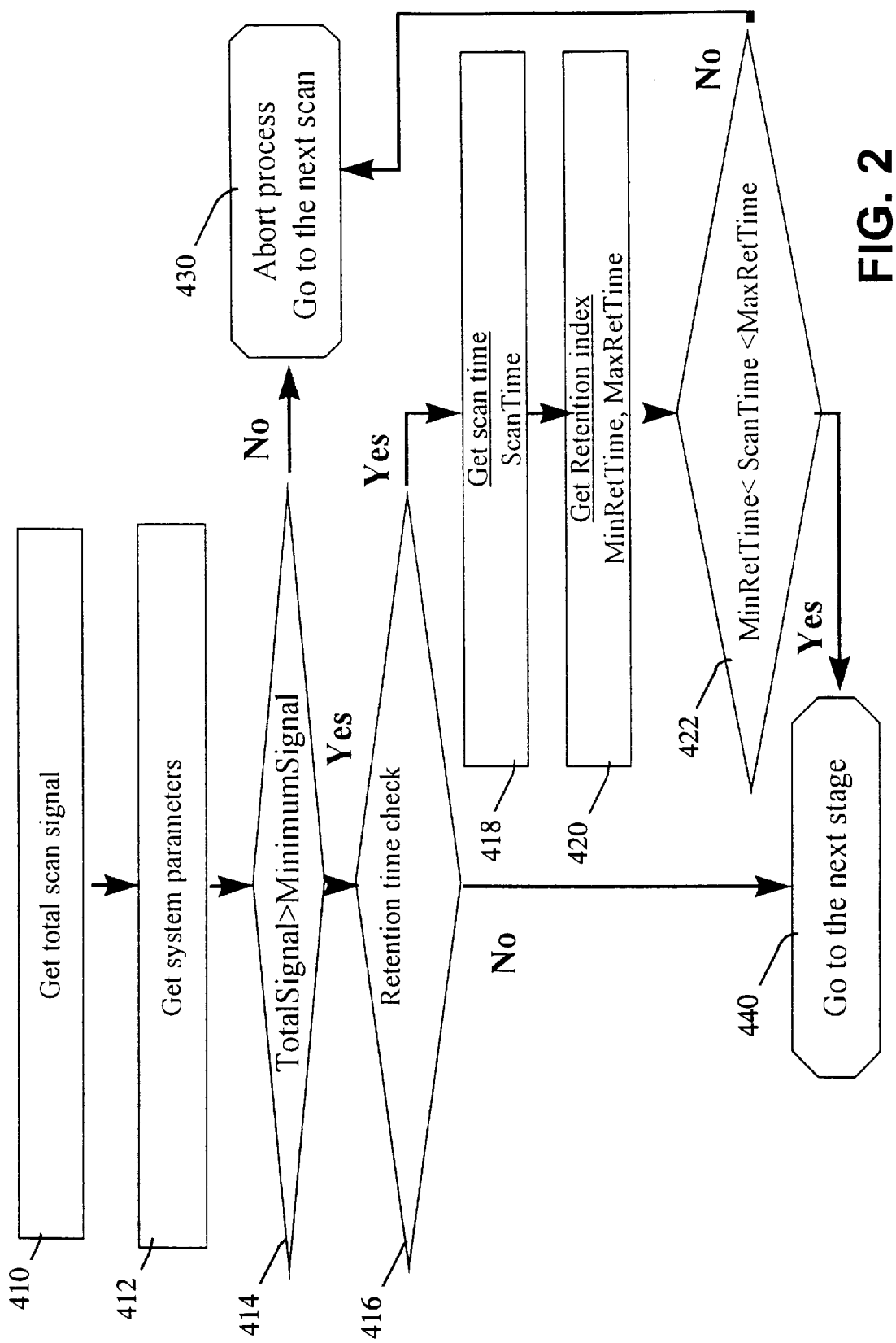
FIG. 2 is a flow chart of the scan analysis Spectral Extraction Module of FIG. 1.

As shown in FIG. 2, the Spectral Extraction module 400, obtains a total scan signal (410) from a computer memory, and compares the total signal (414) to a minimum threshold signal determined by the operator and obtained from a parameter library (412). If the total signal is less than the minimum signal, the scan is ignored (430), and the system moves to analyze the next scan. If a retention time check is not enabled (416), the scan information is passed to the Spectral Line Search module, e.g., ion search in MS, of the Spectral Extraction module 400.

If the retention time check is enabled, the method obtains a scan time (418) based on the actual time the scan was made, and a retention index from a parameter library (420). The retention index is based on the minimum and maximum time at which a given compound can exit the separation unit (if used), e.g., a gas chromatograph, before entering the spectral analysis unit, and is the ratio of the retention time of a target compound over the retention time of an internal standard compound known not to exist in the sample.

The method then compares the scan time and the retention index (422), and considers the scan only if it occurred within the retention index range, i.e., between the maximum and minimum retention times. This is a method of excluding or identifying certain compounds from detection based on their separation time. This step is not required, but can be used with a chromatographic step if desired.

Figure 3:
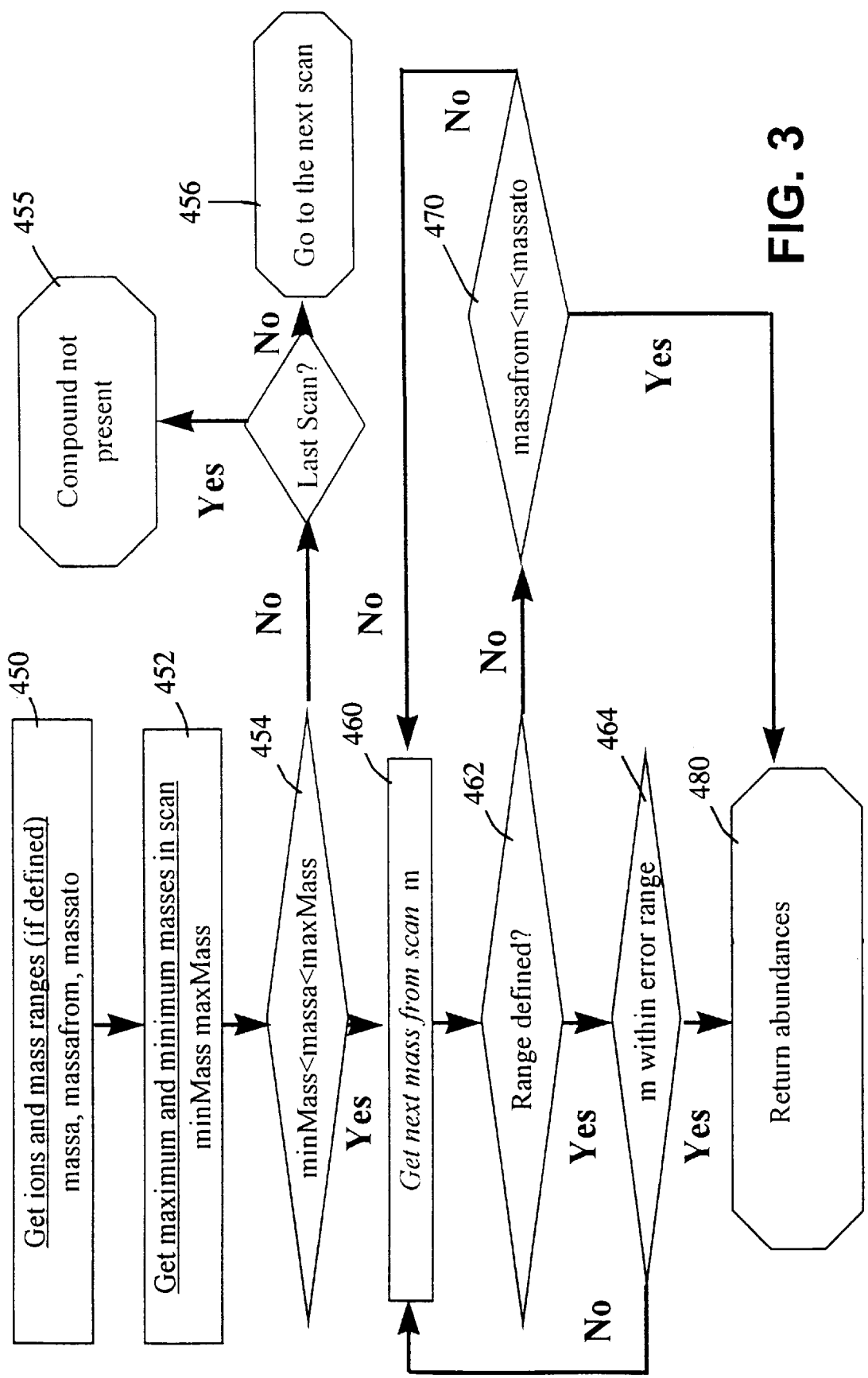
FIG. 3 is a flow chart of the ion search method of Spectral Extraction Module of FIG. 1.

In the Spectral Line Search module within module 400, the method searches the total scan for main and common spectral line positions and quantity values from each of the constituents whose presence in the sample is to be determined. In particular as shown in FIG. 3, for the ion search module in MS, the ion and mass ranges (if defined) are determined from a parameter library table (450) and are compared (454) to detected minimum and maximum mass values found in a particular scan (452). If the range of masses from the look-up table does not fall between the minimum and maximum mass of the actual scan for all scans, then the compound is not present (455). If this is not the last scan, the method continues to the next scan (456). This is another optional technique to exclude certain compounds from detection, again, to improve the overall efficiency of the data analysis method.

In MS, if the masses in the library fall between the minimum and maximum mass of the scan, the system obtains the next mass from the scan (460) and compares it to a defined mass error range (464, if defined, 462). If the mass is within the mass error range, the ion will be used for further analysis in the abundance check (480, and see 510, FIG. 4). If the mass is outside the mass error range, the next mass from the scan is analyzed (460). If the mass error range is not defined, the mass is compared to the mass ranges from the library (470). If the mass is within the library mass range, the ion will be used for further analysis in the abundance check (480), if not, the system obtains the next mass from the scan (460). If the last mass from the scan is obtained, the method moves to the next scan.

Figure 4:
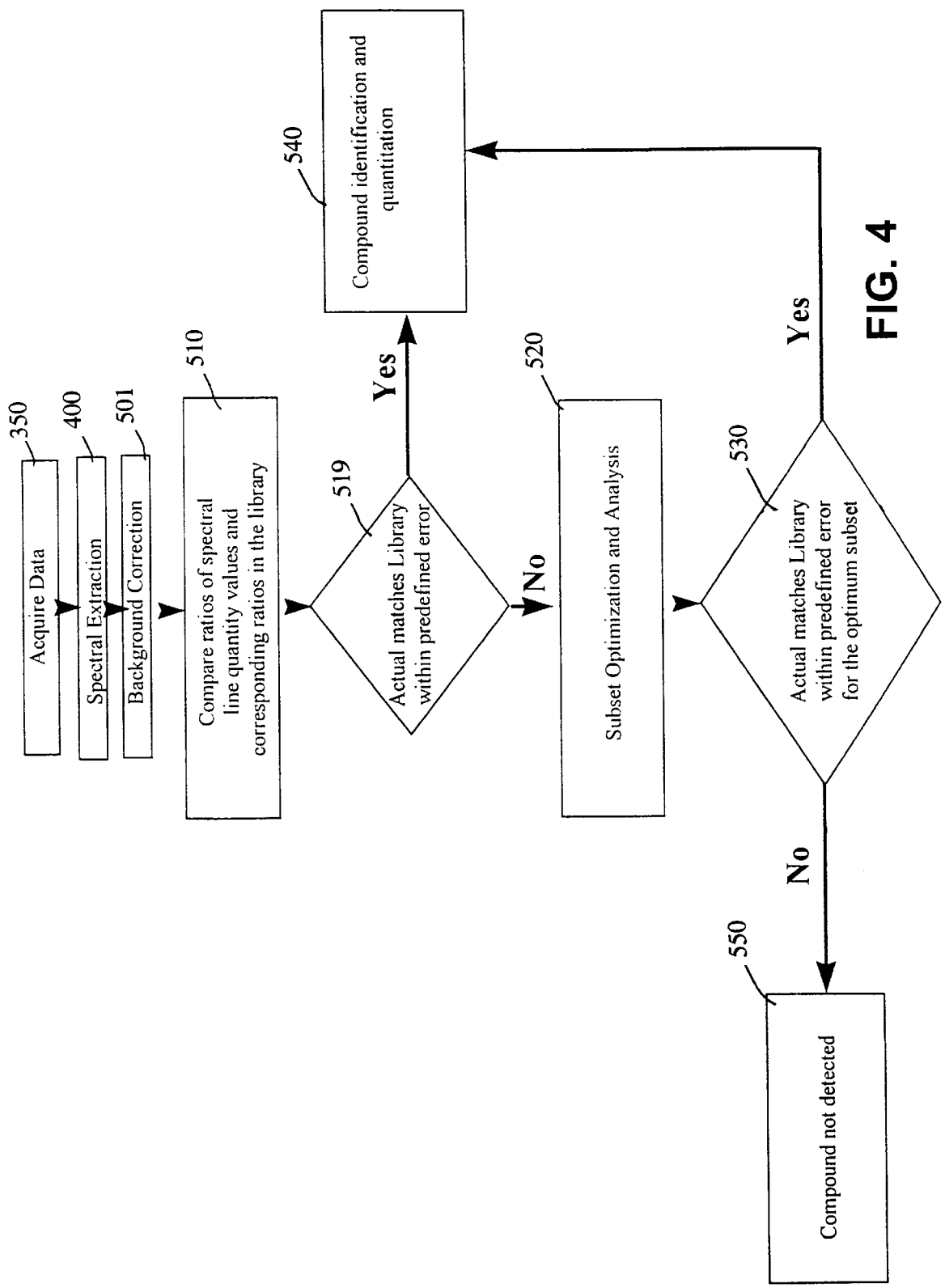
FIG. 4 is a flow chart of the Data Analysis module of the invention.
Figure 5:
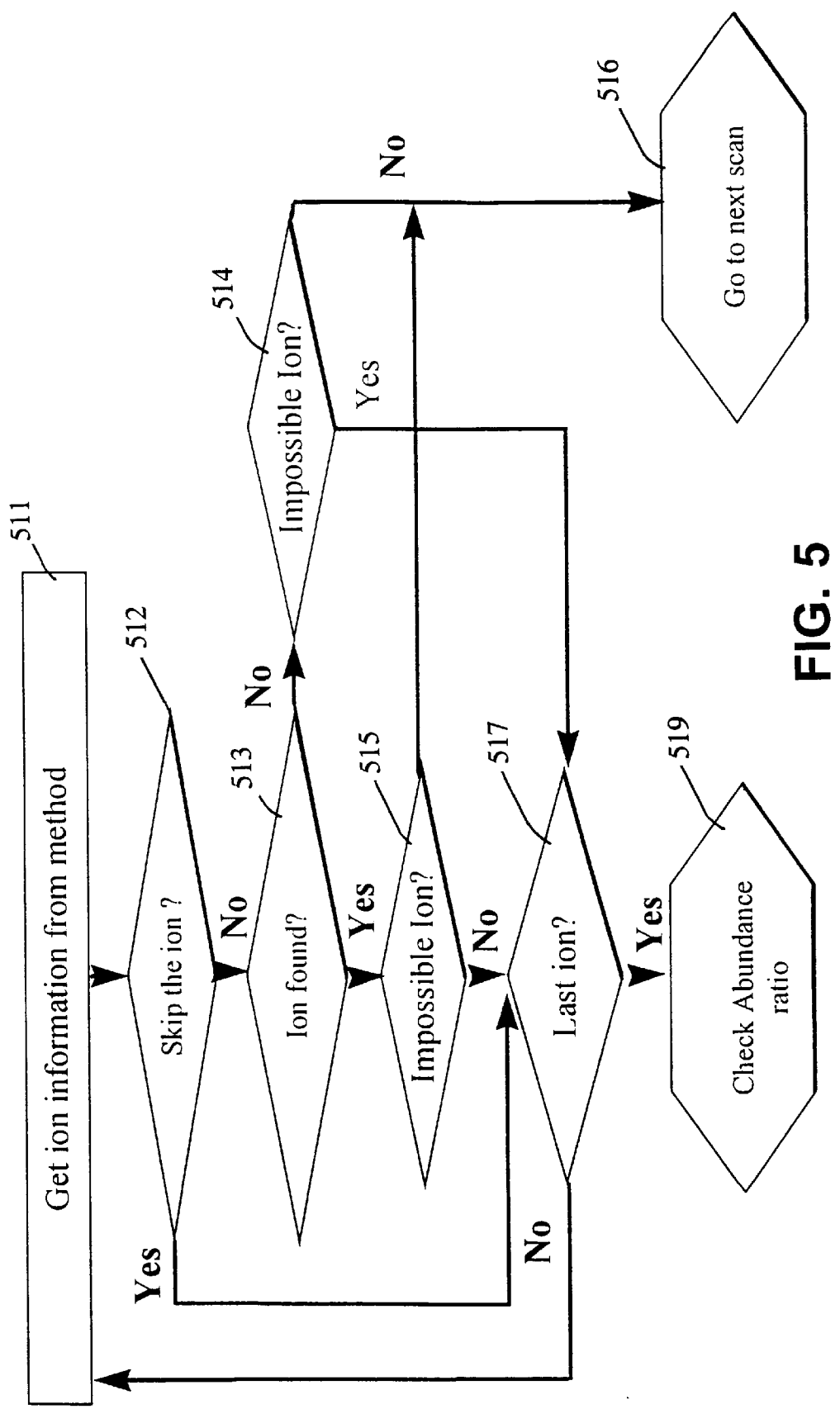
FIG. 5 is the abundance check method of the Data Analysis module of FIG. 4.

As shown in FIG. 4, after the Data Acquisition (350) and Spectral Extraction (400) modules are completed, the data is corrected for background (501), and the sets of relationships, e.g., ratios, of quantity values for the detected constituents are analyzed by comparison to the corresponding ratios in the library (510). In MS, this is referred to as an "abundance check" of the ions found in the ion search step. As shown in FIG. 5, the abundance check is carried out after the system checks the type of ion being analyzed.

As shown in FIG. 5, if an ion is not skipped (512) and is found (513), i.e., falls within mass range and retention index range, the system determines whether the ion is an unacceptable ion (515). An unacceptable ion, or so-called "impossible" ion (FIG. 5), can be defined by the operator as an ion that should not be considered in the spectrum of the targeted compound, see, e.g., Cl-1 (Table 1), in which fragment ion 189 is set manually by the operator to be the unacceptable ion (abundance set to 0%). The unacceptable ion should be selected to be an ion in one target constituent, but in no other. The use of an unacceptable ions works well for most halogen-containing constituents, whereas it is not necessary for PAHs. Note that the use of an unacceptable ion is not necessary for the main steps of the invention.

If the ion is not found, and it is not an impossible ion (514), the system moves to the next scan (516). However, if the ion is not found and is an unacceptable ion, the system checks whether it is the last ion in the scan (517), and if not goes back to the beginning of the loop to obtain the next ion in the scan.

If the ion is found in the scan (513), and is an impossible ion (515), the system moves on to the next scan (516). If the ion is found, and is not an impossible ion (515), the system determines if it is the last ion in the scan (517), and if so, delivers the ion information to the comparison step 510 (FIG. 4). If the ion is not the last ion, the loop continues until the last ion in the scan is analyzed.

Returning now to FIG. 4, the ratios of detected quantity values of spectral lines present in the scan are compared to known ratios in quantity values of compounds in the library. When there is an actual match in the library within a predetermined error range (519), the compound is identified, and the information is passed onto the next module for quantification. If one spectral line of a set of lines corresponding to a particular compound is completely absent in all scans, the system determines that a compound is not present in the sample (not shown). However, if a spectral line is present, but not within the predetermined error range, there may be interference from a spectral line from another compound that happens to have the same position, which causes the quantity value to be greater than expected. It is for these examples that the Subset Optimization and Analysis module 520 comes into play.

To make the comparison (510, 519 in FIG. 4), e.g., abundance check in MS analysis, all calculations are made of "possible" spectral lines, e.g., main and common spectral lines. In the following equations for an abundance check in MS analysis, actual abundances are denoted as A[i], library abundances are denoted as S[i]. Library abundances are defined in percentages. The abundance ratio array is calculated using the following equation (1):

$$R[i]=A[i]/A[1], (A[1]\text{-main ion}) \quad (1)$$

where A[1] is the abundance of the main ion, which is assigned 100%. A normalized ratio array is calculated by the following equation (2):

$$N[i]=\text{Log}(A[1])*R[i]/S[i] \quad (2)$$

where N[i] is the normalized ratio array.

The Sum is determined by the following equation (3):

$$\text{Sum}=\Sigma(N[i]-N[j]) \quad (3)$$

where i,j equals 1 . . . n, n—number of ion. The number of differences (ND) is determined by equation (4):

$$ND=n(n-1)/2\text{—number of elements of previous sum} \quad (4)$$

The ratio of the Sum divided by the number of differences (ND) is a measure of the mismatch between the actual and library ratio values (equation 5).

$$\text{Mismatch}=\text{Sum}/ND \quad (5)$$

The mismatch is compared (by an "if, then" logic based on subtraction) to a predetermined error range. Other mathematical relationships describing the mismatch can be used. The differences are given in terms of percentages.

For example, assume that there is one main ion and one common ion used to represent a particular constituent, the common ion gives an actual sample value of 80% of the main ion in the actual scan, and the library indicates that it should be 70% of the main ion. If the error range is plus or minus 15% for that constituent, then the method determines that the constituent is present in the sample, i.e., the ratio of Sum/ND (equation 5) is within the predetermined error range (519) (FIG. 4). If the error range is only 10%, then the method would determine that there may be interference, and the information is passed to the Subset Optimization and Analysis module 520 as shown in FIG. 4 and detailed in FIG. 6.

Subset Optimization and Analysis

This method is based on the assumption that at least one of the selected spectral lines representing a particular constituent has interference from a spectral line from some other constituent. The system proceeds to examine in turn, all possible subsets of spectral lines while omitting, in each subset, a different line. It evaluates the ratios related to those subsets and determines whether, within an allowed variance, a subset indicates the presence of the constituent of interest. Note that the success of the method is based on the fact that not all of the selected spectral lines have overlapping spectral lines from other compounds that cause interference in the comparison of a particular constituent.

In the case where the main spectral line has interference, it is ignored and does not appear in the subset. In this case, the system assigns a common spectral line to be the new main spectral line and then calculates the ratio of quantity values between the new main spectral line and all of the common spectral lines. The mismatch for the new subset is calculated as shown in the equation above. If the mismatch is within the operator predetermined error range, the system calculates and stores the interference value ("variation" in FIG. 6). The system then finds the spectral line in the new subset with the minimum interference, eliminates the excessive signal due to interference, and recalculates the concentration based on the main ion.

Figure 6:
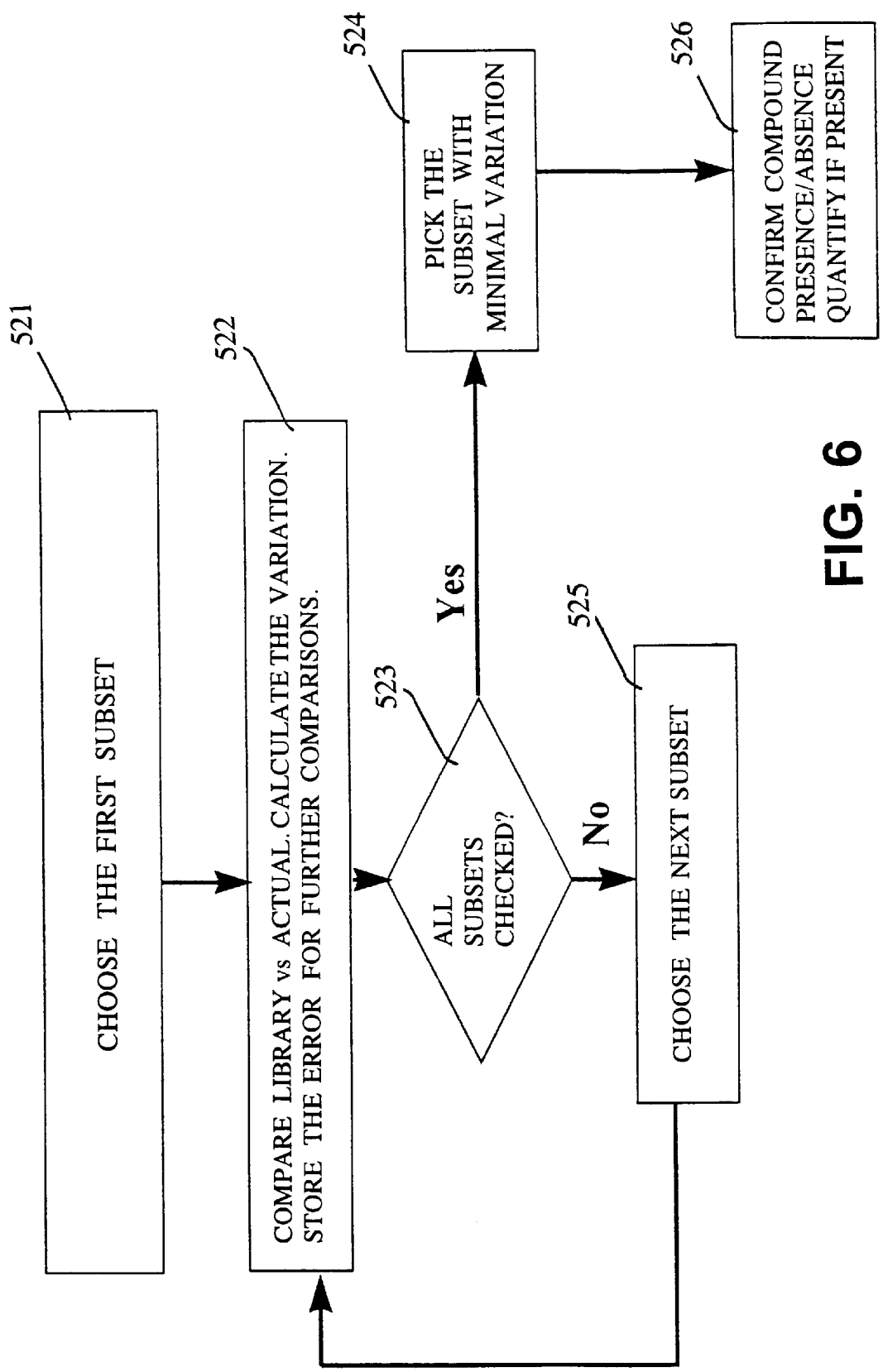
FIG. 6 is a flow chart of the Subset Optimization and Analysis module of the Data Analysis module of FIG. 4.

As shown in FIG. 6, in step 521, a first subset of spectral lines used to represent a particular constituent, e.g., based on ions in MS, is selected, which excludes one spectral line from the initial N spectral lines. Typically, the first subset will include all spectral lines except the first, the second subset will include all lines except the second, and so on.

In step 522, the subset of spectral lines is compared to the same subset of spectral lines in the library, and the variation (mismatch) between them is calculated and stored for further comparisons. In step 523, the system queries whether all subsets have been checked. If so, the subset with the minimal variation value is picked (step 524) and the compound's presence is confirmed in step 526. If all subsets have not been checked (step 523), the next subset of ions is selected (step 525).

For example in MS analysis of an organic compound, if four ions are used to represent a particular compound, the first subset can include ions 2, 3, 4, excluding ion 1, the second subset could be ions 1, 3, and 4, with ion 2 excluded, and so on. In essence, every common ion is assigned to be the main ion, and the entire protocol is repeated. The system attempts to find the subset that gives the smallest variation between the ratios observed in the scan and the ratios stored in the library to determine which of the ions has interference.

After the system processes the data based on the condition that one of the spectral lines of the selected group has interference, i.e., by going through each of the possible subsets, and that does not produce a combination of ratios with an error smaller than the predetermined error ratio, the search is stopped indicating the compound is not present, or it can proceed to a second stage of iterations where the condition is that two of the selected spectral lines have interference and the method is repeated. The number of iterations is determined by the operator.

Two methods have been developed to identify the compound based on the above designation, i.e., "forward analysis," which involves adjusting library spectral line intensities (example below), and "backward analysis" (FIG. 6a), which calculates and adjusts the actual spectral line intensities.

Example of Matrix Calculations—"Forward Analysis"

Assuming that there is one compound to be detected in a sample, and that four ions are used to represent that compound, the following example can be made. A matrix is established from the library values for selected fragment ions for the compound to be detected in the sample. A second matrix is established representing the data for one scan. These matrices are established as follows:

$$\begin{bmatrix} m_1 \\ m_2 \\ m_3 \\ m_4 \end{bmatrix} \quad \begin{matrix} \text{Library} \\ \begin{bmatrix} A_1 \\ A_2 \\ A_3 \\ A_3 \end{bmatrix} \end{matrix} \quad \begin{matrix} \text{Scan Value} \\ \begin{bmatrix} 0 \\ 0 \\ 0 \\ 0 \end{bmatrix} \end{matrix}$$

After obtaining the library and scan data, calculated scan ratios are entered into the library matrix, and actual scan values are entered into the scan matrix as follows (a third matrix contains the percentage of error):

$$\begin{bmatrix} m_1 \\ m_2 \\ m_3 \\ m_4 \end{bmatrix} \quad \begin{matrix} \text{Calculated} \\ \text{Scan Value} \\ \begin{bmatrix} 100\% \\ 90\% \\ 50\% \\ 60\% \end{bmatrix} \end{matrix} \quad \begin{matrix} \text{Scan} \\ \text{Value} \\ \begin{bmatrix} 1000 \\ 1200 \\ 500 \\ 600 \end{bmatrix} \end{matrix} \quad \begin{matrix} \text{Error} \\ \begin{bmatrix} 0\% \\ 25\% \\ 0\% \\ 0\% \end{bmatrix} \end{matrix}$$

Assuming an error range of plus or minus 10 percent for each of the four ions, it is determined that not all of the four ions fall within the error range compared to the library. Therefore, subset optimization and analysis is required and the first subset of ions is chosen that ignores $m_1$. Therefore, a new library matrix is established in which $A_1$ is determined to be unknown, $A_2$ is set to 100%, $A_3$ is set to 50/90 (55.6%), and $A_4$ is set to 60/90 (66.7%). The recalculated scan ratios based on the library values and the recalculated scan values based on the actual values are shown below:

$$\begin{bmatrix} m_1 \\ m_2 \\ m_3 \\ m_4 \end{bmatrix} \quad \begin{matrix} \text{Recalculated} \\ \text{Scan Ratio} \\ \begin{bmatrix} - \\ 100\% \\ 55.6\% \\ 66.7\% \end{bmatrix} \end{matrix} \quad \begin{matrix} \text{Recalculated} \\ \text{Scan Value} \\ \begin{bmatrix} - \\ 1200 \\ 666.7 \\ 800 \end{bmatrix} \end{matrix} \quad \begin{matrix} \text{Error} \\ \begin{bmatrix} - \\ 0 \\ 33.3\% \\ 33.3\% \end{bmatrix} \end{matrix}$$

Assuming in the second iteration that ion $m_2$ has interference, the system considers $m_2$ to be unknown. The matrices are shown below:

$$\begin{bmatrix} m_1 \\ m_2 \\ m_3 \\ m_4 \end{bmatrix} \quad \begin{bmatrix} 100\% \\ - \\ 50\% \\ 60\% \end{bmatrix} \quad \begin{bmatrix} 1000 \\ - \\ 500 \\ 600 \end{bmatrix} \quad \begin{bmatrix} 0\% \\ - \\ 0\% \\ 0\% \end{bmatrix}$$

In the third iteration, ion $m_3$ is considered as an unknown and the matrices are as follows:

$$\begin{bmatrix} m_1 \\ m_2 \\ m_3 \\ m_4 \end{bmatrix} \quad \begin{bmatrix} 100\% \\ 90\% \\ - \\ 60\% \end{bmatrix} \quad \begin{bmatrix} 1000 \\ 900 \\ - \\ 600 \end{bmatrix} \quad \begin{bmatrix} 0\% \\ 25\% \\ - \\ 0 \end{bmatrix}$$

In the fourth iteration, ion $m_4$ is considered as an unknown, and the arrays are as follows:

$$\begin{bmatrix} m_1 \\ m_2 \\ m_3 \\ m_4 \end{bmatrix} \quad \begin{bmatrix} 100 \\ 90 \\ 50 \\ - \end{bmatrix} \quad \begin{bmatrix} 1000 \\ 900 \\ 500 \\ - \end{bmatrix} \quad \begin{bmatrix} 0 \\ 25 \\ 0 \\ - \end{bmatrix}$$

As can be seen from the error matrices, the first condition, that ion $m_1$ has interference, creates the largest error, and the second condition, that ion $m_2$ has interference, creates the lowest error. Therefore, at the end of all four iterations, the subset of ions $m_1$, $m_3$, $m_4$ is used to confirm the compound's presence and the main ion, $m_1$, is used for quantification.

"Backward Analysis"

In the "backward analysis," instead of comparing actual data against library values, the library values are compared against the actual values and the values in the library matrix are adjusted. In essence, the program compares the values in the two matrices, so the order of which is considered "first" does not matter.

An additional means of confirming constituent identity is to repeat the data analysis method for different scans of the same constituent. Each scan of a spectrometer covers a particular point in time, typically on the order of one second apart. Therefore, there are numerous scans taken for each constituent. The data analysis method takes advantage of this fact by making three or more separate analyses of data from different scans that represent the same constituent, e.g., that are of the same peak in a total ion current chromatogram in MS, or at steady-state atomic emission in atomic spectroscopy. When the method repeats itself, the system requires that the criteria, e.g., the quantity values of three of four selected spectral lines must be in the correct ratios, be met in a certain percentage of scans, e.g., three of four scans or seven of ten. The software has the capability to do up to seven or even ten scans through each chromatographic peak.

Predetermined Error Range

The predetermined error range, established initially as part of a method generation procedure, is used in the Subset Optimization and Analysis module 520, and can be different for each compound. The error ranges are established and stored in the library, one or more error ranges being associated with each compound in the library. In some cases the error range may be plus or minus 10 percent, whereas for other constituents it might be plus or minus 30 percent. For other constituents the ratio values of individual spectral lines may each have their own error range.

The error ranges are determined based on sample-specific analysis for each constituent to be detected. For example, in mass spectrometry, the operator performs a three to five point calibration curve over a wide concentration (e.g., 100 parts per billion, "ppb," to 100 parts per million, "ppm") for all constituents to be detected (using known concentrations) in soil, water, or air, depending on the types of samples to be analyzed. The error ranges will often differ for different samples. For example, in soil, there are many more interfering constituents, so the error ranges may need to be broader than in water or air that have fewer contaminants.

The predetermined error range or ranges of each constituent are then determined by evaluating the mismatch between actual and library ratio values, and determining acceptable values of the error ranges based on an accepted confidence level as a function of sensitivity and false positive and negative identification. The predetermined error ranges are then incorporated into the software of the method in the form of a look-up table that is used for all samples in the future that contain the particular constituents in the particular sample.

The accepted confidence level is set to balance false positives (the method says a constituent is present in the sample when it is not) and false negatives (the method says that a constituent is not present in a sample when it is). The operator must determine which of these two is more important (e.g., in determining constituents at toxic waste sites, it is more important to avoid false negatives), and set the error ranges accordingly. The more false positives that the operator can accept (and thus the fewer false negatives), the wider the error range can be.

The error ranges also are established to obtain the desired sensitivity based on concentration. The error range can be smaller at higher concentrations and larger at low concentrations, because there is less of an effect of the S/N ratio at the higher concentrations. For example, the error range for a particular fragment ion of a particular constituent at 100 ppb may be 20%, while it may be 10% at a concentration of 100 ppm.

Using these factors, the operator can establish a useful error range (or ranges) for each of the constituents to be detected in a sample. These calculations need be done only once for a given constituent in a given matrix, and can then be used for all future sample testing. Moreover, with future testing, the results can be used to fine-tune the error ranges through an iterative process.

For example, error ranges useful for the analysis of the following constituents in contaminated soil are provided in Table 2 (below). In Table 2, the error range is applied to each of the ratios of the main ion paired with each of the common ions. The main and common ions for these compounds can be found in Table 1.

TABLE 2

| Compound | Error Range |
| --- | --- |
| naphthalene (PAH) | 25% |
| fluorene (PAH) | 15% |
| Cl-3 (PCB) | 20% |
| Cl-4 (PCB) | 20% |
| Aldrin (Cl-pesticide) | 20% |
| 4,4'-DDT (Cl-pesticide) | 15% |

Background Subtraction

In the example described above for MS, background subtraction can be accomplished in the following manner. For direct MS measurements, MS scans are taken prior to sample introduction and the resulting scan values are subtracted from the actual MS measurements of the sample.

When separation devices such as a chromatograph are employed upstream of MS, there are several standard methods of background subtraction. For example, several scans are taken prior to and after a sample peak in a chromatogram, and the average signals are used as a background signal. Alternatively, all background on the chromatogram excluding the peaks can be averaged and subtracted from the signal of the compound. All of these are known methods of background subtraction and can be applied to other spectroscopic techniques covered by this application.

Concentration

In the present data analysis method, concentration is determined based on the quantity value of one of several, e.g., four, spectral lines used to identify the constituent. Typically, the main spectral line is used for this analysis. The detected quantity value, e.g., ion current in MS analysis, of the main spectral line is used to measure the concentration of the constituent in the mixture. Concentration is generally determined by comparing the absolute abundance (intensity) of the target constituent to the absolute abundance of an internal standard added to the mixture.

The main spectral line typically has the highest quantity value of the four lines used for constituent identification. If the main spectral line, e.g., fragment ion current in MS analysis, is the spectral line that cannot be adjusted within the required error range for the particular constituent due to interference, the system uses one of the other three spectral lines to identify the constituents. Thereafter, the main spectral line is set to a corrected quantity value relative to the quantity value ratios between the main spectral line and the other three lines based on the known ratios for that constituents. Those ratios are fixed based on the correct relative ratio for the constituent and are stored in the library.

An internal standard signal is used to determine the concentration of a constituent, and to insure that the data has been properly sampled. An internal standard is a compound known not to exist in a particular sample, and is added by the operator in a known concentration. For example, if it is known that at equal concentrations a certain compound will produce twice as large a signal as the internal standard, then the operator knows that upon addition of 100 nanograms of the internal standard, a signal from that compound twice as large as the signal of the internal standard indicates that the compound is present at about 100 nanograms in the sample.

Apparatus

The new method of data analysis can be used to analyze data generated by any spectral analysis device that produces narrow band peaks, e.g., including mass spectrometers, fourier transform infrared spectrometers, x-ray fluorescence spectrometers, atomic emission spectrometers. Any type of mass spectrometer filters can be used, including, for example, quadrupole, ion trap, time-of-flight, magnetic sector, ion cyclotron resonance, and fourier transform MS. High resolution MS filtering can be achieved by combining any two or three different (or same) MS filters listed above in series.

The method will work to detect and quantify constituents in any sample, including air, soil, and water. The specific application of the data analysis method is demonstrated below employing a mass spectrometer using a new thermal desorber unit and gas chromatograph containing a short fused silica capillary column upstream of the mass spectrometer.

Other separation methods and devices can be used upstream of the MS, including electrophoresis, membrane separation, etc. However, the new data analysis method is so sensitive and accurate, that for the first time, separation of the constituents in a complex, contaminated mixture prior to spectral analysis is not required, and a sample can be gasified and input directly into the spectral analyzer, e.g., MS.

Mass Spectrometry Analytical System

Any mass spectrometer can be used with the described data analysis method, for example, Hewlett-Packard (Palo Alto, Calif.), Varian (Palo Alto, Calif.), Finnigan (San Jose, Calif.), and Viking Instruments (Chantilly, Va.).

In this application a new thermal desorber gas chromatograph/mass spectrometer (TDGC/MS) system, that incorporates the data analysis method (software) described herein, is capable of detecting up to 125 compounds simultaneously using the total ion current mode of existing MS. The acquired signals are sent to the data analysis module and calculated against expected relative abundances with and without background subtraction. After each compound's fragment ions are normalized against their relative intensities and the current produced by fragment ions not associated with the targeted compound(s) discarded, the actual current due to each compound present in the sample is retained in a separate data file. The data analysis method automatically calibrates compound signal against internal standard and sends the result along with sample weight, extraction efficiency, solvent volume, and moisture content to a standard spreadsheet that directly calculates the compound concentration.

Figure 7:
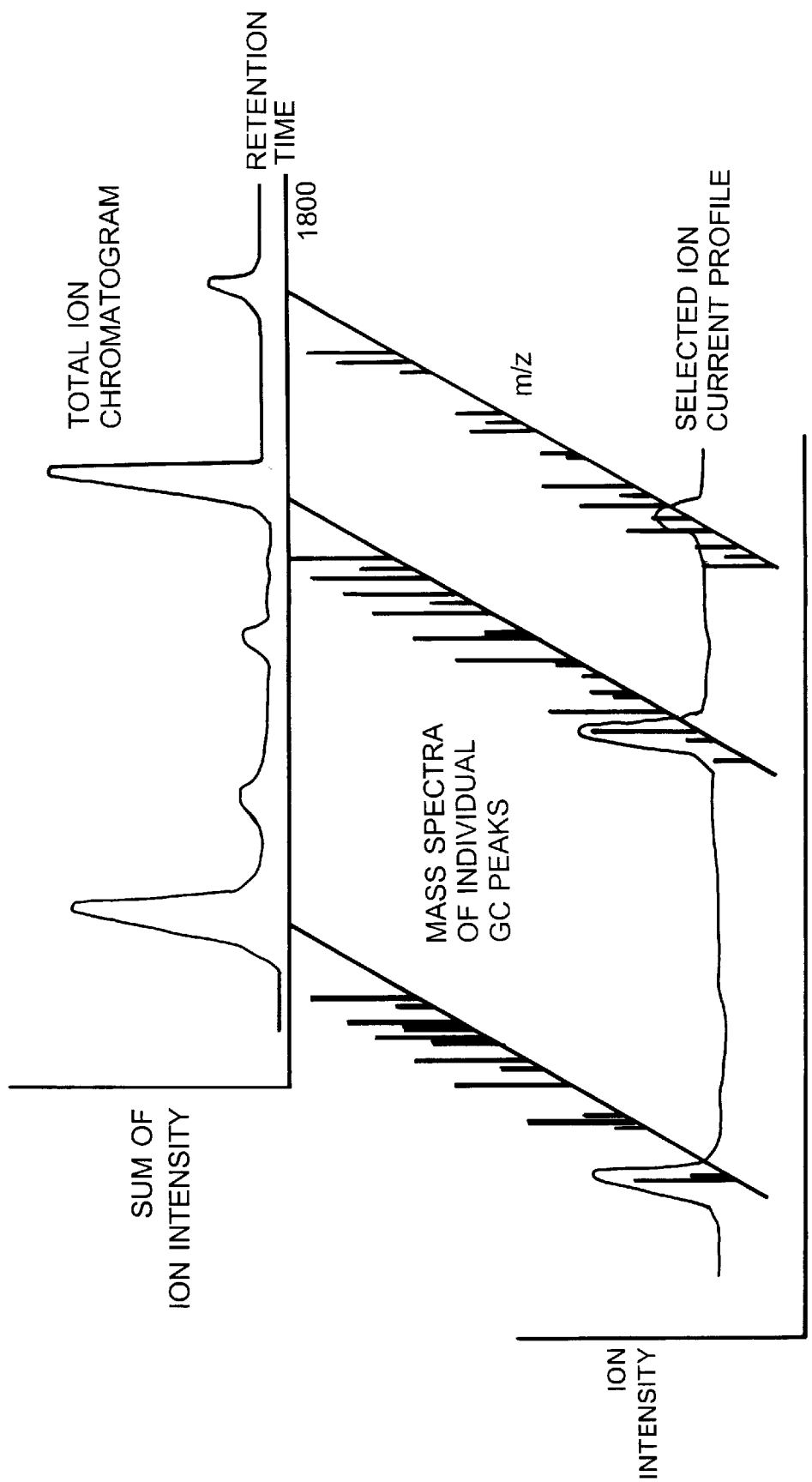
FIG. 7 is a three-dimensional schematic diagram illustrating a total ion current (TIC) chromatogram for a simple mixture, the mass spectra of individual gas chromatograph peaks, and a selected ion current profile.

Results obtained with the new TDGC/MS in terms of linear dynamic range and minimum amount detected, and when used to analyze a PCB/oil contaminated soil sample fortified with PAH and Cl-pesticides are presented below. FIG. 7 shows a schematic total ion current (TIC) chromatogram. The TIC chromatogram is the sum of ion intensity versus retention time. Each of the peaks in the TIC chromatogram is separated into a fragmentation pattern which shows the mass spectral lines of the individual gas chromatographic peaks. This is shown diagonally in FIG. 7, to indicate the temporal relationship of the separate graphs.

FIG. 7 also shows a selected ion current profile which is based on selected ion extraction from the TIC chromatogram. Selected ion monitoring (SIM) employing a single ion per compound provides only a single piece of information and therefore cannot provide unambiguous identification of a particular organic compound. However, the mass spectra obtained from an SIM/MS analysis where several selected ions per compound are detected, e.g., 3 or 4 selected ions known to exist in a particular organic compound, give information sufficient to identify the compound. Prior art devices can monitor up to 20 to 50 ions in the selected ion monitoring mode simultaneously, which limits the total number of compounds that can be analyzed at once to a maximum of about 12. As more sophisticated devices are developed, the number of ions that can be monitored in the SIM will increase, and the SIM will allow the present software method to obtain accurate results even more quickly.

In a complex sample such as an environmental sample, e.g., contaminated soil or water, about 20 percent of the organic compounds present are unambiguously identified in a typical GC/MS analysis employing prior art compound identification software. However, the other 80 percent are only tentatively identified, because of overlapping or interfering fragmentation patterns. The prior art addresses this overlapping problem by performing extensive sample preparation, such as solid phase and liquid extraction and/or gel chromatography, that attempts to separate the individual compounds according to a characteristic property such as size, weight, chemical class or chemical functionality.

Thermal Desorber Unit

Figure 8A:
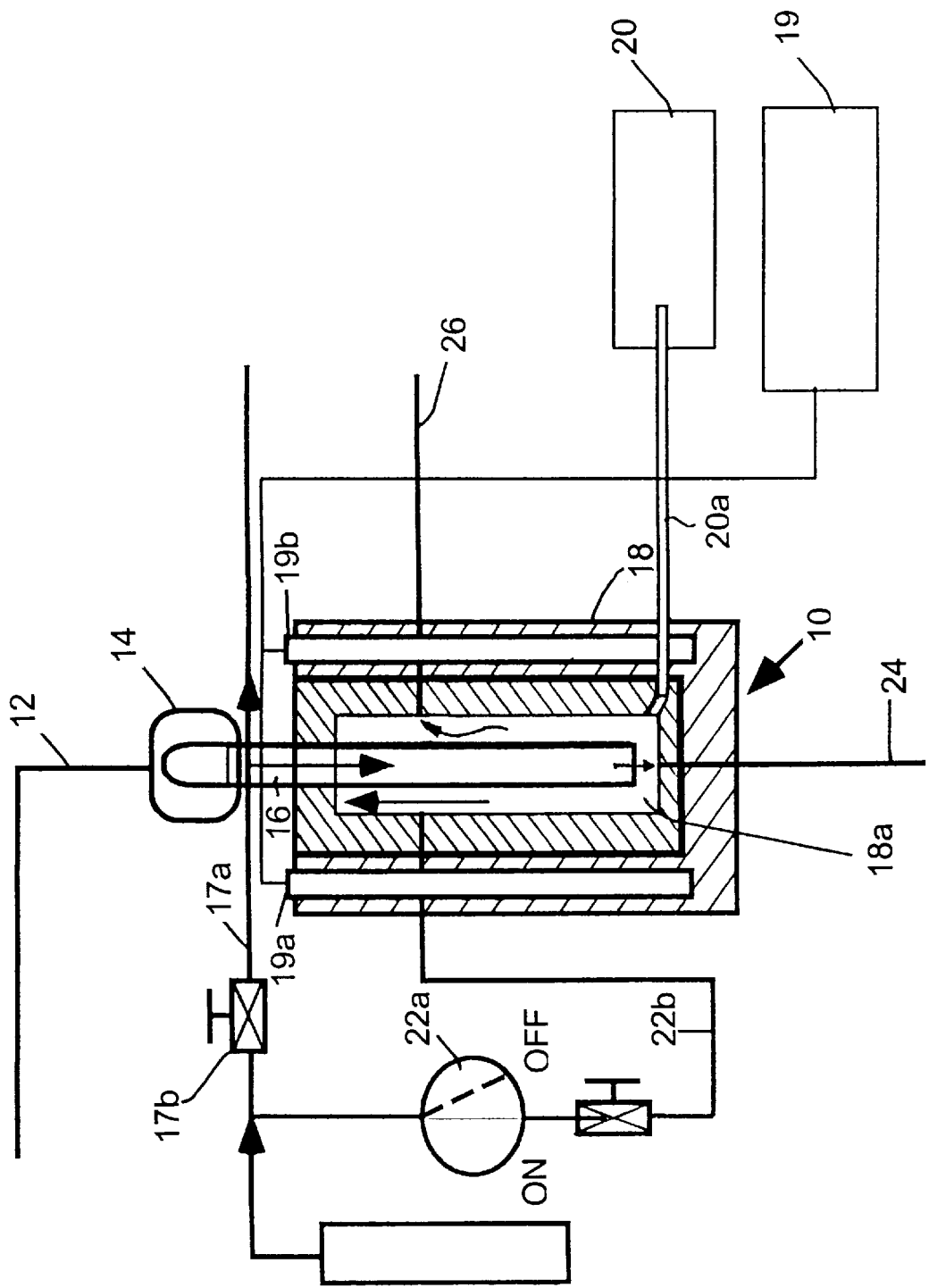
FIG. 8a is a schematic diagram of a new cryogenically cooled thermal desorber (TD) unit.

FIG. 8a shows a new cryogenically cooled/thermal desorber unit 10 capable of introducing solid, liquid, or gaseous materials directly into any gas phase analytical detection device such as a mass spectrometer. The sample can be introduced into the unit in two ways. If the sample is a gas, it can be introduced directly into quartz sleeve 16 via conduit 12, e.g., from a remote sampling location. If the sample is a solid or a liquid, it is introduced directly through an opening covered by removable cap 14. Solid or liquid samples are initially placed into a quartz sleeve 16 and the sleeve is placed into cooled and heated chamber 18.

The plumbing is configured in such a manner that the carrier gas, e.g., nitrogen, helium, or air, sweeps vaporized constituents, such as organic compounds, from chamber 18 into the gas phase detector. Carrier gas enters chamber 16 at two locations via conduits 17a and 22b. Flow in conduit 17a is regulated by a total flow control valve 17b, while flow in conduit 22b is regulated by a blow solenoid valve 22a. These two valves regulate flow of the carrier gas into the thermal desorber and into any gas chromatograph (GC) that may be used upstream of the gas phase detector. The gas always flows into the GC, but flows into chamber 18 only when the sample is ready to be flushed into the gas phase detector. The high volume of carrier gas typically used to flush the sample into the detector is too high for the GC, therefore when the sample is being cooled or heated in the TD, the gas flow to the GC can be split to reduce the net flow to the GC (e.g., 1, 5, or 10%), with the remainder going to atmosphere. The remainder is passed into the TD during flushing.

Two separate exit conduits (24 and 26) allow the use of two separate gas phase detectors, e.g., an MS, and an electron capture detector that detects only halogenated constituents.

For solid samples, where an organic extract of a sample has been prepared, the volatile solvents must be removed before the extract is introduced into the gas phase detector, e.g., MS, because these solvents swamp the detector and make any results meaningless. Thus, the temperature of chamber 18 is initially set to a low temperature (e.g., 25° C.) that vaporizes only the volatile solvents, and a first flush of carrier gas is used to carry these volatile solvents out of the device to the atmosphere while the semi-volatile constituents cling or adhere to the inner walls of sleeve 16. The sleeve is then ballistically heated (e.g., rapid heating to high temperatures, for example, as fast as 10 or 15 seconds or less) with heater cartridges 19a and 19b within the walls of chamber 18 to a temperature of at least 300° C. or higher to vaporize the semi-volatile constituents, which are then carried into the gas phase detector by a new flush of carrier gas. Power supply 19 supplies electricity to the heaters 19a and 19b.

In another embodiment, when the device is used to sample gases with a probe that extends dozens to hundreds of feet from the TD, high volumes of a carrier gas are required to move the sample this distance, but can dilute the sample to the point below the level of detection of the gas phase detector. Thus, low temperature cooling, e.g., cryogenic cooling, is used to cool chamber 18, and thus quartz sleeve 16, to a temperature (e.g., −30° C.) at which organic constituents to be detected in the gaseous sample are frozen onto the inner wall of the sleeve, while the carrier gas is cooled, but not frozen or liquified, and can be drawn out of the sleeve and the chamber, e.g., by an air sampling vacuum pump. In particular, liquid nitrogen, or other coolant, from tank 20 is fed into the inside 18a of chamber 18 via conduit 20a to rapidly cool the chamber. The liquid nitrogen is removed via the same conduit, or via another exit port.

After the carrier gas is removed, the chamber is slowly heated to room temperature, and then ballistically heated as described herein. Both of these heating phases are accomplished by the heater cartridges 19a and 19b that are located within the walls of chamber 18. These cartridges are electric resistance heaters, and are connected to an electric power supply 19. The now concentrated, vaporized organic constituents are then introduced into the gas phase detector by a normal flush of carrier gas.

The new data analysis method and thermal desorption unit were combined into a new TDGC/MS instrument. This new instrument is able to identify individual constituents within various compound classes in under 7 minutes total time. As shown in FIG. 8b, the TDGC/MS 30 is small and light weight (32 Kg and 78×49×34 cm). The GC houses two different sample introduction systems: (1) a standard split/splitless syringe injection port (shown at 32); and (2) a Pyrex lined inlet sleeve (34) (o.d. 8 mm, i.d. 6 mm, length 99 mm) to which the thermal desorber described above was attached. The thermal desorber can be ballistically heated from ambient temperature to 320° C. in about 45 seconds. In this study, the thermal desorption temperature was held constant at 300° C. for 45 seconds while the volatilized constituents were swept into the head of column 38 by the carrier gas, He; at a flow rate of 66 cm/sec and a head pressure of 8 psi. The GC oven 36 is temperature programmable from 1° C./min. to 100° C./min. and can accommodate a 60 m high resolution fused-silica capillary column. A 15 m, 0.25 mm i.d., 0.25 μm film thickness model HP-5MS (Hewlett Packard, Little Falls, Del.) 5% diphenyl, 94% dimethyl, 1% vinylpolysiloxane capillary column 38 was employed.

As shown in FIG. 8c, the new TD described above enables the use of a MS device without any GC. This TD/MS has a very short conduit between the Pyrex lined inlet sleeve 34 and the electron impact ionization source 40. Thus, the transfer distance for any sample is much less than 12 inches, e.g., 3 inches. This combination allows for the first time the direct introduction of samples into the MS without any prior separation device. The new TD allows increased quantities of sample to be analyzed as compared to syringe injection providing MS detection comparable to electron capture detection for both PCBs and chlorinated pesticides.

Two GC temperature programs were utilized: (1) initial temperature 120° C. (2 minutes), temperature programmed from 120° C. to 170° C. at 60° C./min., then to 250° C. at 20° C./min., finally to 320° C. at 70° C./min., followed by a 1.3 minute isothermal period at 320° C. (total elution time 9.4 minutes); and (2) initial temperature 150° C. (1 minute), temperature programmed from 150 to 315° C. at 50° C./min., followed by 1.7 minute isothermal period at 315° C. (total elution time 7 minutes).

The mass spectrometer control electronics were obtained from Hewlett Packard. An active film ETP (Auburn, Mass.) multiplier lead set detector LS515 was used. This unit was better able to withstand high sample background interferants consistent with minimal sample preparation of petroleum based samples. High background sample components were rapidly removed from the MS system by a Varian (Lexington, Mass.) V60 Turbo pump and an oil reservoir. The electron impact ionization source (40 in FIG. 8b) was held at 70 eV nominal with a source temperature of 260° C. The quadrupole mass filter 42 was scanned between 100 amu and 500 amu every second with unit resolution at 10% peak valley. The initial signal threshold was set at 300. At the beginning of each day, the instrument was auto-tuned in the typical manner at masses 69, 219, and 502 utilizing a standard calibration gas, perfluorotributylamine (PFTBA). A power supply 44, and GC electronics 46 are also included within the housing of the unit 30. The data is output to a computer via cable 48.

Hewlett Packard's Mustang-III software was used to control the instrument and acquire the fragment ion current. The new data analysis software described above was used in this device. The software provided compound specification and quantification in the presence of high levels of interferants in the sample. A Method Generator module in the software was used to create either a comprehensive total semivolatile or class-specific method by retrieving from different libraries the respective TDGC/MS experimental conditions as well as the compound(s), their fragment ions and corresponding relative abundances; see Table 1. For example, if only PAHs are to be analyzed, the Method Generator module pulls all information relevant to PAHs from the parameter and compound libraries and puts the information into the proper modules to operate the device and detect the PAHs.

Relative retention times (RRT) produced from a standard solution on a daily basis were placed in the library and compared against the RRTs of the targeted organics. RRTs were used as a second means of compound identification. Once all the information was placed into the compound identification software, the Data Analysis (DA) module 500 was ready to process data. The module determined compound presence by adjusting actual ion current against each compound's normalized abundance ratio after background subtraction as described above.

Figure 8D:
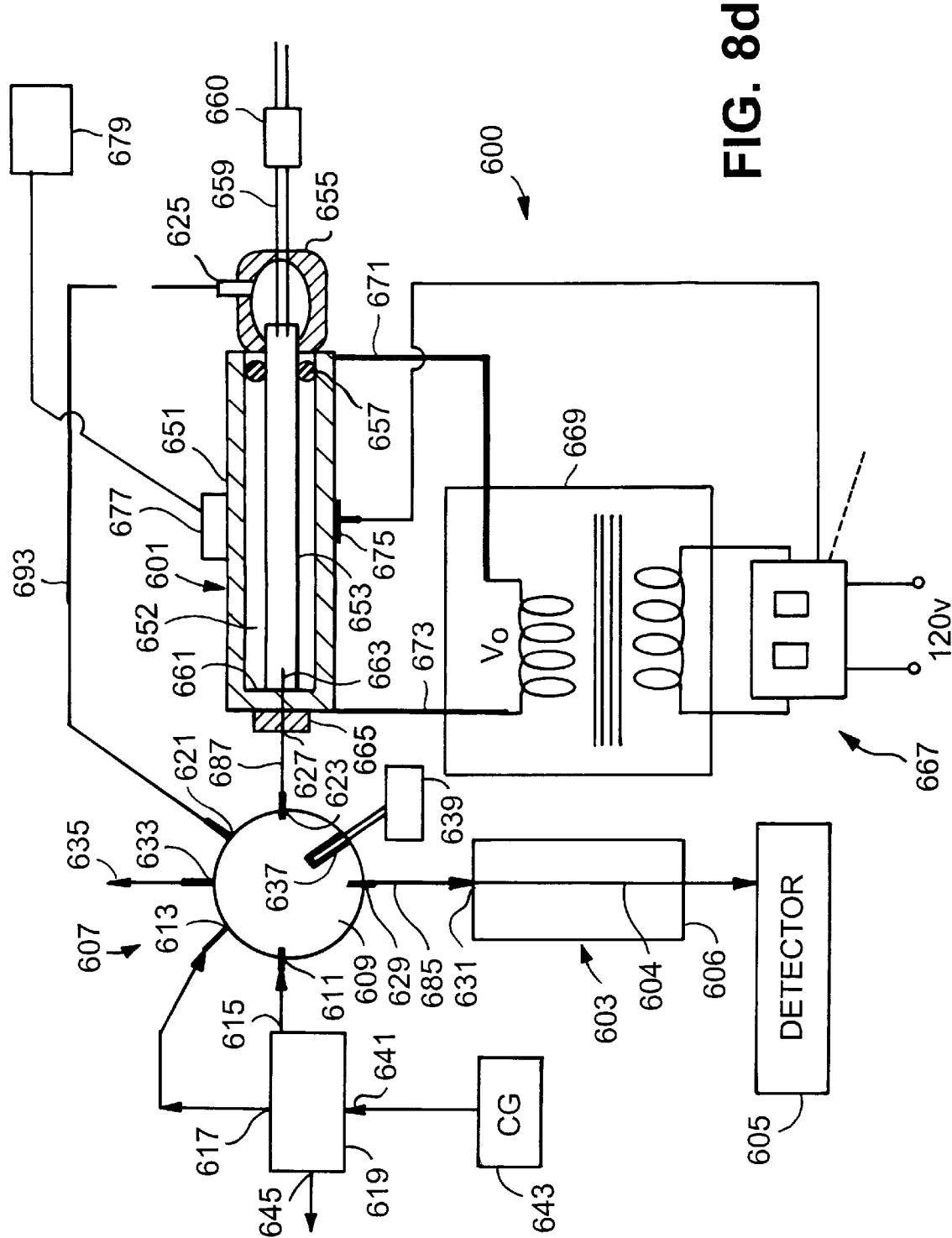
FIG. 8d is a schematic diagram of a gas phase analysis system including a thermal desorber.

Referring now to FIG. 8d, another embodiment of a spectrometry system 600 includes a thermal desorption unit 601 that is coupled to one or more sample analysis instruments via a valve assembly 607. The sample analysis instruments can include a gas phase separator 603, a gas phase detector 605, or both. If both are used, the gas phase separator 603 is arranged in series between the valve assembly 607 and gas phase detector 605, as illustrated in FIG. 8d.

The gas phase separator 603 can be a gas chromatograph (GC) having a GC column 604 inside an oven 606. GC column 604 can include a tube made of fused silica, having an inner diameter of, e.g., 0.10, 0.25, 0.32, or 0.53 mm, and a length of approximately 5 to 60 meters. Other materials and different size columns can also be used, if appropriate. The gas phase separator 603, e.g., a GC, operates essentially as described above with reference to the system illustrated in FIG. 8a. System 600 is particularly adapted to inhibit oxygen from contaminating GC column 604. Although the following description refers primarily to use of a GC for the gas phase separator 603, other instruments can be used instead. For example, a supercritical fluid chromatograph can be used instead of a GC.

Gas phase detector 605 can be a mass spectrometer, a flame ionization detector, a thermal conductivity detector, or the like.

Valve assembly 607 includes an electronically controlled multi-port valve 609. Two ports 611, 613 are coupled to respective outlets 615, 617 of a splitter valve 619 for receiving flows of a carrier gas. Two other ports 621, 623 are respectively coupled to a gas inlet 625 and a gas outlet 627 of thermal desorption unit 601. A fifth port 629 is directly coupled to an inlet of a short length 685 of GC column 604 that extends out from GC oven 606. The short length 685 of GC column can be approximately 5–10 cm long. A sixth port 633 is coupled to an exhaust 635. Valve 609 includes a valve heating system, e.g., a cartridge heater 637 and a power supply/controller 639 for controlling heat to valve 609. Valve 609 can be heated to at least about 325° C.

Splitter valve 619, which is also electronically controlled, is adapted to regulate the flow of a carrier gas and a purge gas through outlets 615 and 617, respectively. An inlet 641 of splitter valve 619 is coupled to a carrier gas (CG) supply 643. The carrier gas also can serve as the purge gas. A third outlet 645 of splitter valve 619 is provided for flushing the line from CG supply 643 to splitter valve 619 and splitting off a flow of the carrier gas from the flow directed to outlets 615 and 617.

Thermal desorber unit 601 is mounted horizontally to permit the system to be used to analyze liquid or solid samples. Thermal desorber unit 601 includes a cylindrical body 651 made of an inert material, e.g. stainless steel. Body has an inner diameter of approximately 8.2 mm, an outer diameter of approximately 10.9 mm and a length of approximately 6–7 cm. Body provides a cylindrical chamber 652 in which a sample holder formed of a desorption tube 653 is positioned. Desorption tube 653 is substantially surrounded by body 651 within chamber 652, and is open at both ends. One end of tube 653, which may extend past the open end of body 651, is covered by a removable end cap 655. The opposite end of desorption tube butts against an interior end surface 661 of body 651. End surface 661 is coated with gold to inhibit interactions with sample gases.

Desorption tube 653 can be formed of a disposable sleeve of glass or any other inert material. It has an inner diameter of approximately 6 mm, an outer diameter of approximately 8 mm, and a length of approximately 6 to 7 cm. Reducing the size of desorption unit 601, by reducing the sizes of body 651 and desorption tube 653, can reduce the dead volume and surface area of desorption tube 653 and also reduce the heat capacity of body, thereby speeding up the rate of a desorption or flushing process. The smaller dead volume will also improve the GC or SFC separation by introducing a tight versus broad band sample. For example, desorption tube 653 can be reduced to a length of approximately 10 mm and an inner diameter of approximately 2 mm, and body 651 reduced commensurately. Various sizes desorption units and desorption tubes can be used for particular samples and situations.

A seal, e.g., an O-ring (not shown), is provided between end cap 655 and body 651. Another O-ring 657 holds desorption tube 653 in place within chamber 652 and also provides a seal between body 651 and desorption tube 653.

End cap 655 includes gas inlet 625. End cap 655 also includes a gas sample inlet, through which a gaseous sample can be introduced into one end of desorption tube 653. The gas sample inlet is provided by a gas sample tube 659 and a shut-off valve 660. Gas sample tube 659 extends through end cap 655 and partially into one end of desorption tube 653. This arrangement allows a gas sample to be introduced into desorption unit 601 through gas sample tube 659 without opening end cap 655.

A tube 687, which is made from the same tubing as GC column 604 and forms a part of GC column 604, extends from valve port 623, through a swage fitting 665, and through end surface 661. An end portion 663 of tube 687 extends into desorption tube 653. The length of tube 687 between valve port 623 and swage fitting 665 is made as short as possible, for example, approximately 1 cm long.

Thermal desorption unit 601 includes a heating system for ballistically heating desorption tube 653. Desorption tube 653 is heated by heating body 651. Body 651 is typically fabricated of metal, e.g., of stainless steel, or other resistive conductor. Body 651 is directly heated by passing a modest, low voltage current directly through it. A power supply/controller 667 includes a transformer 669 for producing a low output voltage $V_O$, which can be approximately one volt. $V_O$ is coupled to body 651 by wires 671, 673, which can be, e.g., copper wires. A thermocouple 675 attached to body 651 is coupled to a feedback circuit in power supply/controller 667 for controlling $V_O$.

This direct heating system can heat the above-described desorption tube 653 from ambient temperature to at least about 325° C. in approximately 6–15 seconds. If the sizes of body 651 and desorption tube 653 are made smaller, the heating time may be reduced even more.

Alternatively, thermal desorption unit 601 can be heated by cartridge heaters, as described above with reference to the embodiment illustrated in FIG. 8a. However, cartridges heat the system more slowly, and take longer to cool down than with the direct heating system.

Thermal desorption unit 601 also has a cooling system, including a solid state cooler 677 and a DC power supply/controller 679, the operation of which is based on the Peltier effect. Solid state coolers are available, e.g., from Pro-Tech (e.g., model number DA-008-05-02). Solid state cooler 677 can be mounted in close thermal contact with body 651, and therefore can cool a body 651, that is sized as described above, from a few hundred degrees Celsius down to approximately ambient temperature in approximately 30 seconds.

Alternatively, a liquid nitrogen cooling system can be used, an example of which is described above in the discussion of the system illustrated in FIG. 8a. When a liquid nitrogen cooling system is used in conjunction with cartridge heaters, the desorber unit 601 can be cooled from a few hundred degrees Celsius down to approximately ambient temperature in a few minutes, approximately 2 to 10 minutes.

Solid state cooler 677 can be run in reverse to heat thermal desorption unit 601. This may be practical for very small thermal desorption units and could eliminate the need for a separate heating system, or at least speed the rate of heating.

As discussed above, a short length 685 of GC column 604 extends between GC oven 606 and valve port 629. Tube 687, which extends between valve port 623 and desorber gas outlet 627. These sections 685, 687 are heated when valve 609 is heated.

Valve assembly 607 has two modes of operation. In a "run mode" illustrated in FIG. 8e, multi-port valve 609 communicatively couples the carrier gas from port 611 to port 621. From there, the carrier gas passes through tube 693 to thermal desorption unit gas inlet 625. Gases are carried by the carrier gas out from thermal desorption unit gas outlet 627, and through tube 687 to port 623. Valve 609 couples port 623 to port 629, allowing the carrier gas to carry the gasses from desorption unit 601 into GC column extension 685. Gasses passing through GC column 604 then can flow into detector 605.

Figure 8F:
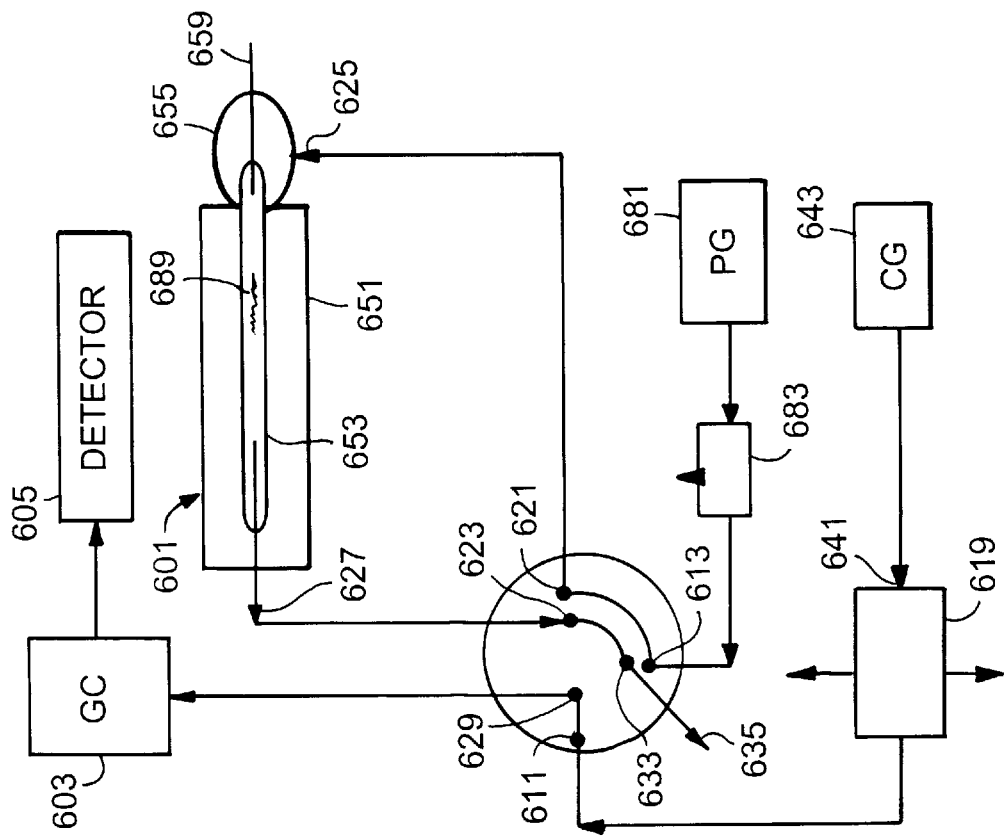
FIG. 8f is a schematic diagram of another mode of operating the system of FIG. 8d.
Figure 8E:
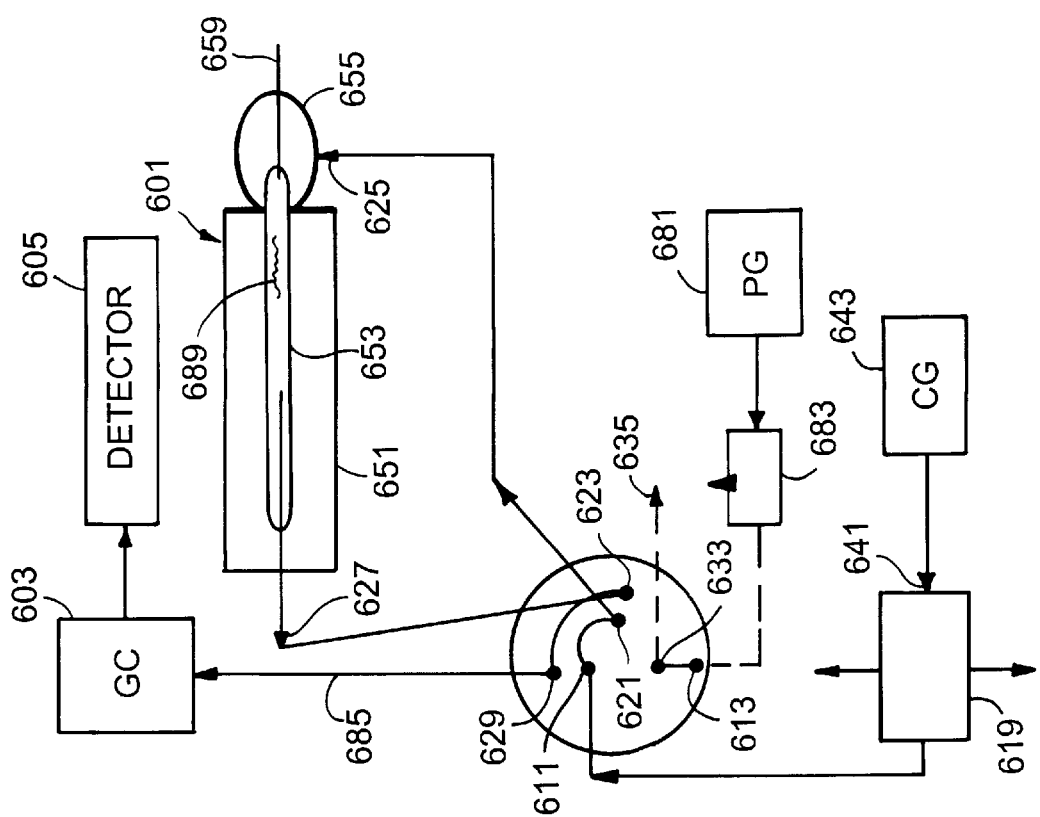
FIG. 8e is a schematic diagram of one mode of operating the system of FIG. 8d.

In a "flush mode" of operation, illustrated in FIG. 8f, the carrier gas flows into valve port 611, which is coupled to port 629. From there, the carrier gas flows into GC column extension 685, through GC column 604, and into detector 605. Carrier gas entering valve 609 through port 613 is communicatively coupled through port 621 and conduit 693 to thermal desorption unit gas inlet 625. Carrier gas flushes other gasses out of thermal desorber unit 601 through gas outlet 627. The flushed gasses flow through tube 687 to port 623. Port 623 is coupled to port 633, so that these gasses can be vented or otherwise pumped away through exhaust 635. In flush mode, a flow of carrier gas continues to flow through GC column 604 and any downstream detector 605, while thermal desorption unit 601 is being flushed with the carrier gas entering valve 609 through port 613. As shown in FIGS. 8e and 8f, the gas used for flushing thermal desorber unit 601 can come from a purge gas supply (PG) 681 that is different from carrier gas supply 643. A separate splitter valve 683 is used to regulate the flow of purge gas.

EXAMPLES

Standard Solutions

The GC/MS linear dynamic range and instrument detection limits (IDL) were determined over a wide concentration range using a standard stock solution of PAHs, PCBs, and organochlorine pesticides. The standard solution was prepared and then serially diluted until each solution's corresponding compound-specific MS signal was no longer observable. The standard stock solution contained 190-ng/$\mu$L total PCB and 200-ng/$\mu$L of each PAH and organochlorine pesticide. The stock solution was prepared from the standards shown below as provided by each supplier: PAH; 2000-ng/$\mu$L each in methylene chloride/benzene (1/1)(Ultra Scientific, Hope, R.I.); total PCB; 1000-ng/$\mu$L in methanol (Supelco, Bellefonte, Pa.); chlorinated pesticides; between 2000 and 2055-ng/$\mu$L each in toluene/hexane (1/1) (Supelco); and pyrene-$d_{10}$; 500 ng/$\mu$L in acetone (Ultra Scientific). Each standard solution was analyzed three times to establish the instrument's linear dynamic range, detection limits, and statistics; see temperature program 1 for instrument operating conditions.

Figure 9:
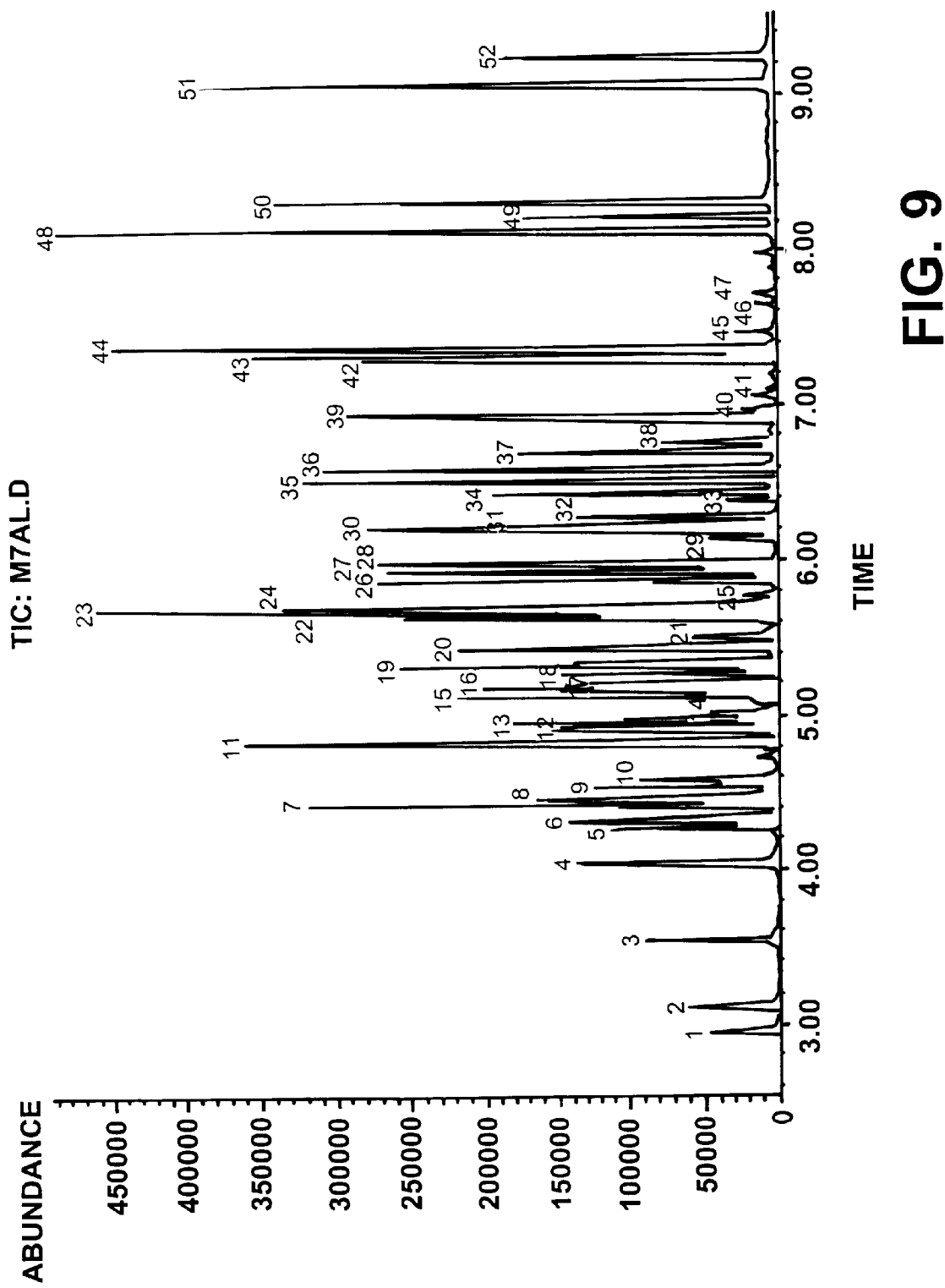
FIG. 9 is a 10-minute TIC chromatogram for a standard solution containing AROCLOR 1248, polycyclic aromatic hydrocarbons (PAHs), and chlorinated pesticides.

FIG. 9 illustrates the total ion current (TIC) chromatogram obtained in under 10-min for the standard solution containing a complex mixture of PCBs (Aroclor 1248, 60 ng total), 16 PAHs (20 ng each), and 16 Cl-pesticides (10 ng each). Note that Aroclor 1248 contains about 55 congeners of which 26 are greater than 1% in concentration. Table 3 below lists the peak numbers, corresponding organics, and the average percent relative standard deviation (% RSD) over the linear dynamic range, as well as the instrument detection limit (IDL). These results are consistent with data obtained from commercially available GC/MS instruments and are based on syringe injection of the standard solutions (n=3 at each of 5 concentrations). Peak 49 corresponds to octachloro-naphthalene, which was used as an internal standard.

Moreover, of the 52 peaks in FIG. 9, 29 peaks contain PCB congeners. Several of the peaks, e.g., peaks 4, 21, 23, and 31 contain either PAH or organochlorine pesticides. Peak clusters 15–19 and 22–24 contain organics that elute so closely that it would be difficult to conclusively identify each compound utilizing conventional MS library matching software. Unlike the data shown here, the prior art requires class-specific range studies, because individual compounds in complex mixtures cannot be unambiguously identified during the short analysis times used herein.

Figure 10:
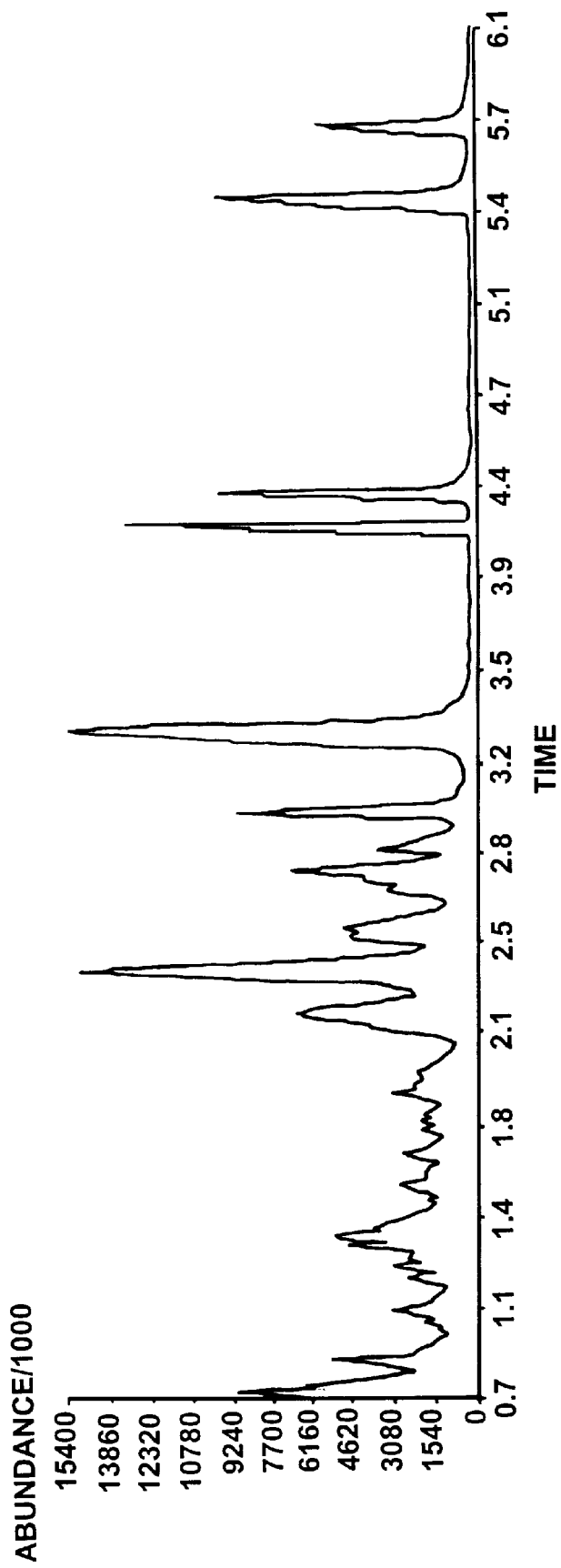
FIG. 10 is a 6-minute TDGC/MS TIC chromatogram of rapid separation of the same standard solution containing AROCLOR 1248, polycyclic aromatic hydrocarbons (PAHs), and chlorinated pesticides used in generating FIG. 9.

As opposed to the nicely resolved 10-min TIC chromatogram of FIG. 9, the TIC chromatogram in FIG. 10 reveals the output of a 6-minute analysis for the same standard solution. The 52 peaks are reduced to about 18 peaks that are much broader and ill-defined. The broad base widths of the peaks indicate that there are multiple components unresolved underneath each of those peaks. However, the data analysis method is capable of separating the 18 peaks into individual constituents contained in the standard solution sample. This is illustrated in the next example.

TABLE 3

| Peak # | Organics | Linear Dynamic | IDL (ng) | % RSD |
|---|---|---|---|---|
| 1 | Acenaphthylene | 1000 - 0.5 | 2.4 | 33 |
| 2 | Acenaphthene | 1000 - 0.5 | 1.8 | 17 |
| 3 | Fluorene | 1000 - 0.5 | 0.6 | 6 |
| 4 | $\alpha$-BHC | 1000 - 0.5 | 0.5 | 9 |
| 4 | PCB (Cl-1) | 950 - 3.7 | 4 | 8 |
| 5 | $\gamma$-BHC | 1000 - 0.5 | 0.5 | 22 |
| 6 | $\beta$-BHC | 1000 - 0.5 | 0.5 | 11 |
| 7 | PCB (Cl-3) | 950 - 3.7 | 4 | 8 |
| 8 | Phenanthrene | 1000 - 0.5 | 0.6 | 16 |
| 9 | PCB (Cl-3) | 950 - 3.7 | 4 | 8 |
| 10 | PCB (Cl-3) | 950 - 3.7 | 4 | 8 |
| 11 | PCB (Cl-3) | 950 - 3.7 | 4 | 8 |
| 12 | PCB (Cl-3) | 950 - 3.7 | 4 | 8 |
| 13 | Heptachlor | 1000 - 0.5 | 1.6 | 32 |
| 13 | Endosulfan sulfate | 1000 - 0.5 | 1.2 | 24 |
| 14 | PCB (Cl-4) | 950 - 3.7 | 4 | 8 |
| 15 | PCB (Cl-4) | 950 - 3.7 | 4 | 8 |
| 16 | PCB (Cl-4) | 950 - 3.7 | 4 | 8 |
| 17 | PCB (Cl-4) | 950 - 3.7 | 4 | 8 |
| 18 | Aldrin | 1000 - 0.5 | 1.4 | 12 |
| 19 | PCB (Cl-4) | 950 - 3.7 | 4 | 8 |
| 20 | PCB (Cl-4) | 950 - 3.7 | 4 | 8 |
| 21 | PCB (Cl-4) | 950 - 3.7 | 4 | 8 |
| 21 | Endosulfan 1 | 1000 - 0.5 | 0.53 | 7 |
| 22 | PCB (Cl-4) | 950 - 3.7 | 4 | 8 |
| 23 | PCB (Cl-4) | 950 - 3.7 | 4 | 8 |
| 23 | Fluoranthene | 1000 - 0.5 | 0.7 | 18 |
| 24 | PCB (Cl-4) | 950 - 3.7 | 4 | 8 |
| 25 | PCB (Cl-5) | 950 - 3.7 | 4 | 8 |
| 26 | PCB (Cl-4) | 950 - 3.7 | 4 | 8 |
| 27 | Pyrene | 1000 - 0.5 | 1.3 | 25 |
| 28 | PCB (Cl-5) | 950 - 3.7 | 4 | 8 |
| 29 | PCB (Cl-5) | 950 - 3.7 | 4 | 8 |
| 30 | 4,4' DDE | 1000 - 0.5 | 0.7 | 14 |
| 31 | PCB (Cl-5) | 950 - 3.7 | 4 | 8 |
| 31 | Dieldrin | 1000 - 0.5 | 0.65 | 13 |
| 32 | PCB (Cl-5) | 950 - 3.7 | 4 | 8 |
| 33 | PCB (Cl-6) | 950 - 3.7 | 4 | 8 |
| 34 | Heptachlor epoxide | 1000 - 0.5 | 0.39 | 8 |
| 35 | PCB (Cl-5) | 950 - 3.7 | 4 | 8 |
| 36 | 4,4' DDD | 1000 - 0.5 | 1.6 | 31 |
| 37 | Endrin aldehyde | 1000 - 0.5 | 0.9 | 27 |
| 38 | PCB (Cl-5) | 950 - 3.7 | 4 | 8 |
| 39 | 4,4' DDT | 1000 - 0.5 | 0.53 | 11 |
| 40 | PCB (Cl-6) | 950 - 3.7 | 4 | 8 |
| 41 | Endosulfan 2 | 1000 - 0.5 | 0.6 | 16 |
| 42 | Endrin ketone | 1000 - 0.5 | 0.7 | 14 |
| 43 | Benzo[a]anthracene | 1000 - 0.5 | 0.57 | 11 |
| 44 | Chrysene | 1000 - 0.5 | 1.2 | 20 |
| 45 | PCB (Cl-7) | 950 - 3.7 | 4 | 8 |
| 46 | PCB (Cl-7) | 950 - 3.7 | 4 | 8 |
| 47 | PCB (Cl-6) | 950 - 3.7 | 4 | 8 |
| 48 | Benzo[b]fluoranthene | 1000 - 0.5 | 0.5 | 10 |
| 48 | Benzo[k]fluoranthene | 1000 - 0.5 | 0.5 | 10 |
| 50 | Benzo[a]pyrene | 1000 - 0.5 | 0.5 | 11 |
| 50 | Indeno[1,2,3-cd]pyrene | 1000 - 0.5 | 0.5 | 10 |
| 51 | Dibenz[a,h]anthracene | 1000 - 0.5 | 0.6 | 16 |
| 52 | Benzo[g,h]pyrene | 1000 - 0.5 | 0.5 | 14 |

Soil Samples

The data analysis method eliminated the masking effect of interferant fragment ions in the soil samples that would normally require extensive sample cleanup. This was evidenced by excellent measurement precision and accuracy for different PCBs, PAHs, and Cl-pesticides at both low (20–60 ppb) and high (20–60 ppm) concentrations in highly complex oil-contaminated soil samples. Moreover, compound identification and quantitation was accomplished without the need for prior fractionation of the sample and without the need to obtain baseline separation of organics.

Our initial field methods included a 5 minute/sample preparation step followed by a 40 minute TDGC/MS analysis to determine the concentrations for all three classes of compounds in one sample run. Total sample preparation and analysis time for the twenty samples was 13 hours, and, compared against the known enzyme kits, the TDGC/MS provides compound specification with truer estimates of concentration at about the same production rate.

To establish the method detection limit (MDL) for each compound measured in the presence of high levels of sample interferants, an oil-contaminated soil sample was obtained from a large scale pumping station located at a Kentucky Superfund site. Analysis indicated that this soil sample contained 60±25 ppm PCB. The PCB concentration was determined by employing EPA method 8080. The soil sample was fortified to contain 60 ppm of each PAH and 20 ppm of each organochlorine pesticide. Then, an aliquot of the soil was serially diluted 10, 100, and 1000 times with the same soil collected from the site. The oil contaminated soil used for dilution was found to contain no detectable PCBs.

Since the signal to noise ratio for the diluted soil containing 60 ppb of total PCBs, 60 ppb of each PAH, and 20 ppb of each organochlorine pesticide was no less than 3 for each compound, this soil was used to determine the MDL. The MDL was calculated as follows based on Environmental Protection Agency, Appendix B to Part 136—Definition and Procedures for the Determination of the Method Detection Limit—Revision 1.11, pp. 565–567.

$$MDL = t_{(n-1, \alpha=0.99)} S \qquad (6)$$

where $t_{(n-1, \alpha=0.99)}$ is the Students' t test value at the 99% confidence level, and S is the standard deviation for n=7. The original PCB contaminated oil sample fortified to contain 60 ppm of each PAH and 20 ppm of each organochlorine pesticide was used to determine measurement precision and accuracy.

Soil samples were prepared for analysis by extracting 2 g of soil with 4 mL of acetone in a hand shaken (3 minutes) TEFLON®-lined screw cap 7 mL sample vial. The supernatant was removed from the vial after centrifuging for 5 minutes and placed in a 2 mL amber glass vial along with 15 ng/µL of the internal standard, pyrene-d$_{10}$. The samples were analyzed according to temperature program 2. The analyte concentration was calculated as follows:

$$C_x = (A_x C_{is}) / (A_{is} RF_x W_s) \qquad (7)$$

where, $A_x$ is the target analyte signal (ion current); $C_{is}$ is the known concentration of the internal standard (ng injected); $A_{is}$ is the corresponding internal standard signal (ion current); $W_s$ is the weight of the sample; and $RF_x$ is the MS response factor which equals $(A_{std} C_{is})/(A_{is} C_{std})$ where $C_{is}$ and $C_{std}$ are the known (ng injected) concentrations of the internal standard and target analyte while $A_{is}$ and $A_{std}$ are the signals of the internal standard and target analyte, respectively.

Results of the TDGC/MS for 100-uL of the 1000 fold diluted soil extract (60 ppb PCB and PAH, 20 ppb Cl-pesticides each) are shown in Table 4 below. Evident from the S/N data is the fact that many of the compounds can be detected at concentrations below the MDL shown in the table. The quality of data produced in seven minutes with minimal sample cleanup by the new TDGC/MS and data analysis method is as good as that produced by standard laboratory instruments and methods where each compound family is typically analyzed in a separate analysis (not all at once as by the present system) and over much longer time periods.

TABLE 4

| Compound | Signal/Noise | % RSD | MDL, ppb |
|---|---|---|---|
| PAHs: | | | |
| Naphthalene | 3 | 36 | 67 |
| Acenaphthylene | 13 | 24 | 46 |
| Acenaphthene | 23 | 23 | 44 |
| Fluorene | 14 | 36 | 68 |
| Phenanthrene | 50 | 46 | 87 |
| Anthracene | 50 | 38 | 72 |
| Fluoranthene | 451 | 36 | 68 |
| Pyrene | 46 | 19 | 35 |
| Chrysene | 2511 | 53 | 99 |
| Benzo(a)anthracene | 1311 | 33 | 62 |
| Benzo(b&k)fluoranthene* | 2139 | 55 | 104 |
| Benzo(a)pyrene | 5 | 33 | 61 |
| Chlorinated Pesticides: | | | |
| BHC-α | 5 | 23 | 15 |
| BHC-β | 9 | 37 | 23 |
| BHC-δ | 7 | 28 | 18 |
| BHC-γ | 4 | 22 | 14 |
| Heptachlor | 11 | 39 | 24 |
| Aldrin | 20 | 26 | 16 |
| Heptachlor epoxide | 27 | 38 | 24 |
| Endosulfan 1 | 4 | 32 | 20 |
| Dieldrin | 9 | 39 | 25 |
| 4,4' DDE | 29 | 19 | 12 |
| Endosulfan 2 | 40 | 28 | 18 |
| 4,4' DDD | 29 | 35 | 22 |
| Endosulfan sulfate | 66 | 26 | 16 |
| 4,4' DDT | 31 | 13 | 8 |
| Endrin | 10 | 33 | 21 |
| Endosulfan aldehyde | 10 | 32 | 20 |
| Endrin ketone | 10 | 35 | 22 |
| PCBS: | | | |
| Cl-3 total | 15 | 36 | 68 |
| Cl-4 total | 14 | 34 | 63 |
| Cl-5 total | 10 | 37 | 69 |
| Cl-6 total | 58 | 36 | 68 |
| Cl-7 total | 7 | 25 | 48 |

In Table 4, the * denotes total of both isomers.

Figure 11:
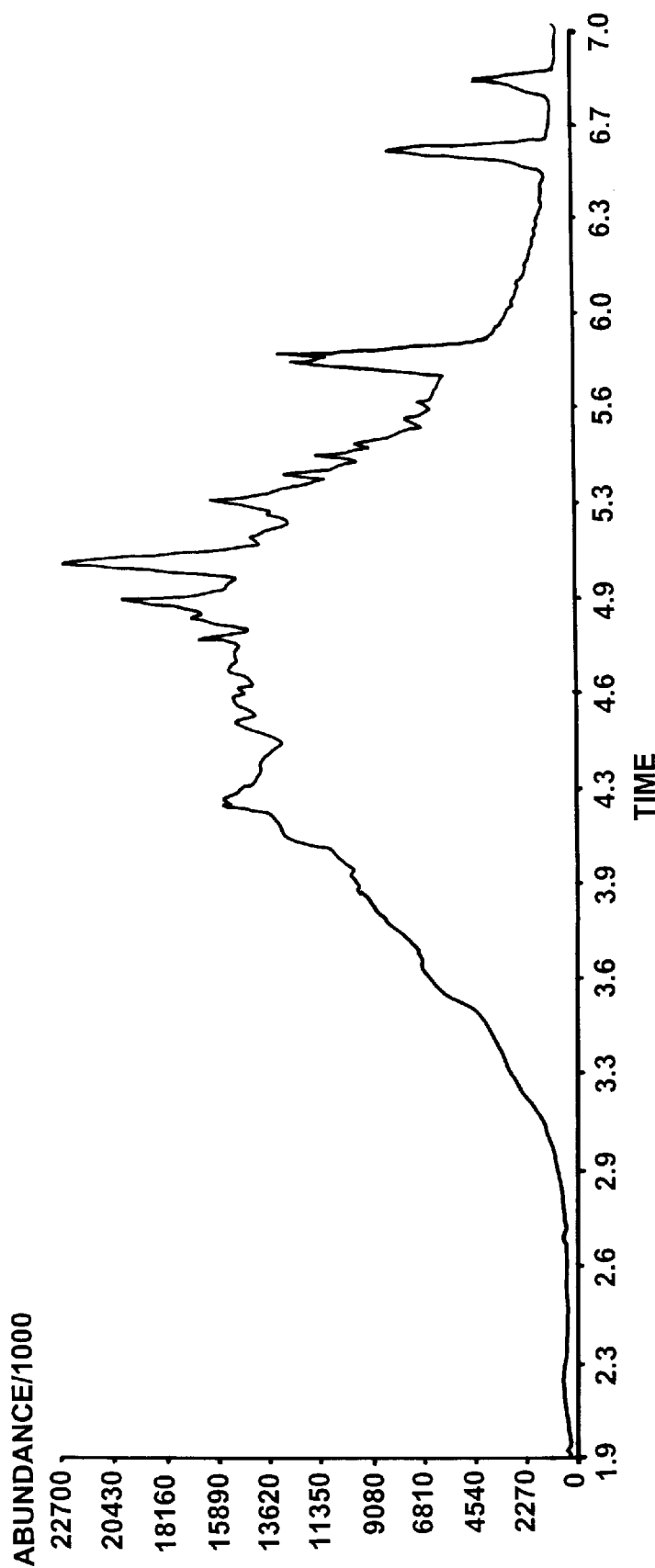
FIG. 11 is a 7-minute TDGC/MS TIC chromatogram for an extract of a fortified contaminated soil sample containing polychlorinated biphenyls (PCBs), PAHs, and chlorinated pesticides.
Figure 12:
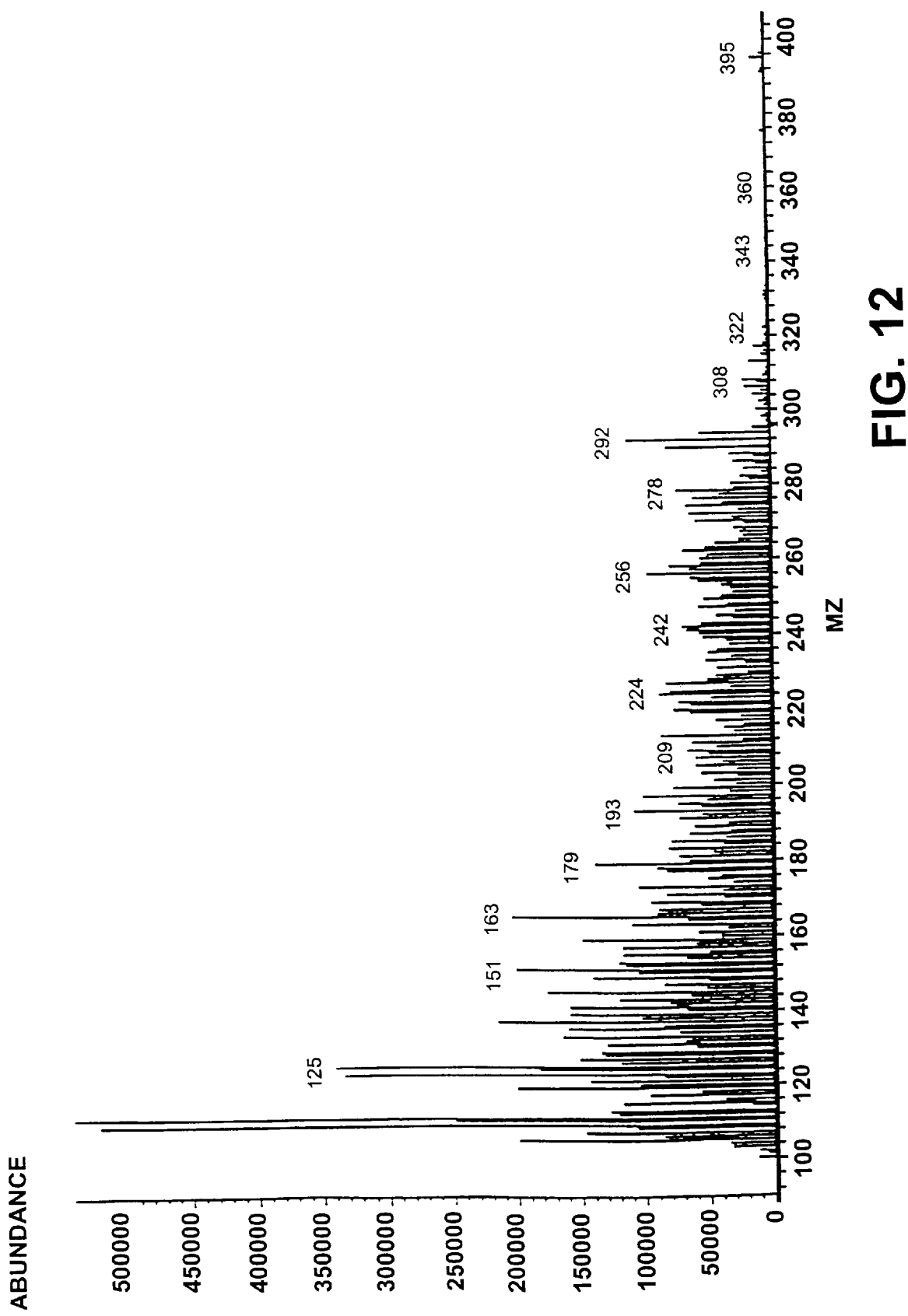
FIG. 12 is an MS spectrum of the TIC chromatogram of FIG. 11 at 4.9 minutes, where a target compound, tetrachlorinated biphenyl, coelutes with another target compound, heptachlor epoxide, as well as other organic compounds present in an oil-contaminated sample.

The undiluted PCB/oil contaminated soil sample fortified with the PAH and Cl-pesticides was analyzed to determine instrument performance under the most adverse conditions. Based on the assumption that the contaminated oil has approximately 300 organic compounds, and that each organic compound has about 6 fragment ions, this sample would have approximately 2500 fragment ions between 2.9 minutes and 7 minutes. FIG. 11 illustrates a 7-minute TIC chromatogram for an extract prepared from this sample. At 4.9 minutes, tetrachlorinated biphenyl coelutes with heptachlor epoxide producing the shoulder of the peak at 5.0-min. The mass spectrum of the TIC chromatogram of FIG. 11 at 4.9 minutes is shown in FIG. 12. The mass spectrum of the TIC chromatogram for tetra-chlorinated biphenyl run as a clean sample with no other compounds is shown in FIG. 13. This distinct pattern of spectral lines is hidden in the hundreds of spectral lines, with many interfering lines, shown in FIG. 12. The software of the invention allows this jumble of lines to be analyzed and allows the principal organic compounds to be identified and quantified. Further, this analysis is accomplished by analyzing only 3 to 5 spectral lines that represent each compound (which may have a 10, 20, or more total spectral lines).

Table 5, below, depicts the measurement precision and accuracy for the 60 ppm PCB/oil contaminated soil sample fortified to contain 60 ppm of each PAH and 20 ppm of each Cl-pesticide (n=3). "Precision" is an indication of the repeatability of the analysis, and "accuracy" is the absolute value of the percent difference between results of analysis of the method and known values, i.e., how close the results of the method were to the actual concentration. Measurement precision and accuracy all fall within the 30% EPA Contract Laboratory requirements for all targeted compounds with the exception of dieldrin (accuracy 41%) and well within the 40% field analysis benchmark, established in past Superfund projects for acceptable quality field data (Robbat et al., *Hazardous Waste and Hazardous Materials,* 10:461–473, 1993).

TABLE 5

| Compound | Concentration ppm | Precision % RSD | Accuracy \|% Diff\| |
|---|---|---|---|
| PAHS: | | | |
| Naphthalene | 59 | 6 | 2 |
| Acenaphthylene | 58 | 5 | 3 |
| Acenaphthene | 56 | 2 | 7 |
| Fluorene | 56 | 2 | 7 |
| Phenanthrene | 55 | 1 | 8 |
| Anthracene | 55 | 4 | 8 |
| Fluoranthene | 54 | 4 | 10 |
| Pyrene | 54 | 4 | 10 |
| Chrysene | 56 | 5 | 7 |
| Benzo(a)anthracene | 50 | 22 | 25 |
| Benzo(b&k)fluoranthene* | 110 | 5 | 9 |
| Benzo(a)pyrene | 50 | 2 | 25 |
| Indeno(1,2,3-cd)pyrene | 47 | 7 | 22 |
| Dibenz(a,h)anthracene | 48 | 3 | 21 |
| Benzo(g,h,i)perylene | 45 | 17 | 25 |
| Chlorinated Pesticides: | | | |
| BHC-α, β, and δ* | 47 | 1 | 22 |
| BHC-γ | 17 | 6 | 15 |
| Heptachlor | 18 | 15 | 1 |
| Aldrin | 17 | 6 | 15 |
| Heptachlor epoxide | 17 | 13 | 15 |
| Endosulfan 1 | 17 | 7 | 15 |
| Dieldrin | 12 | 21 | 41 |
| 4,4' DDE | 20 | 22 | 1 |
| Endosulfan 2 | 15 | 13 | 25 |
| 4,4' DDD | 18 | 24 | 1 |
| Endosulfan sulfate | 16 | 13 | 20 |
| 4,4' DDT | 17 | 20 | 15 |
| Endrin | 18 | 21 | 1 |
| Endosulfan aldehyde | 16 | 7 | 20 |
| Endrin ketone | 21 | 1 | 5 |
| PCBs: | | | |
| Cl-3 total | 8 | 31 | |
| Cl-4 total | 27 | 20 | |
| Cl-5 total | 14 | 21 | |
| Cl-6 total | 2 | 35 | |
| Cl-7 total | 4 | 7 | |
| total | 69 | 11 | 15 |

In Table 5, * designates the total of all isomers.

The system described above with reference to FIGS. 8d–8f can be used for analyzing gas, liquid and solid samples. Gas samples taken from sources such as, for example, hot stack gas emissions or on-line monitors, can be analyzed without contaminating GC column 603 with oxygen. First, with end cap 655 sealed on body 651 and desorption tube 653 in place in body 651, and with valve 660 to gas sample inlet 659 shut off, valve assembly 607 is placed in the flush mode. Thermal desorber unit 601 is cooled by cooling unit 677 to a temperature well below ambient temperature, for example, to approximately −20° C.–0° C. Valve 660 is opened to introduce the gas sample into chamber 653 via sample gas inlet 659. Volatile and semi-volatile organics in the hot gas sample condense onto the inner wall of the cooled desorption tube 653. Valve 660 is then closed. The sample is accumulated in desorption tube 653, while other gaseous components that do not condense at the cooled temperature, such as oxygen, are safely flushed out through the exhaust.

The valve assembly is then switched to run mode. At about the same time, the GC 603 and detector 605 are started up, and thermal desorption unit 601 and valve 609 are heated. Desorption tube 653 is ballistically heated to a desorption temperature that is selected based upon the volatility of a target constituent. Alternatively, virtually all organic condensates can be desorbed by heating to a temperature above about 300° C., e.g. approximately 325° C.

Using the direct heating method, desorption tube can be heated to the selected temperature in about 6–12 second or less. This flash desorbs the condensate in desorption tube 653. The organic vapors are carried through valve 609 onto GC column 604. The temperature is maintained at the desorption temperature for the time it takes for the carrier gas to completely move the desorbed gasses out from desorber tube 653 and into CG column 604. Assuming a desorber tube volume of approximately 6–8 ml, and a carrier gas flow rate of approximately 2–3 ml per minute, this time is approximately 2–4 minutes.

The valve assembly is then placed in flush mode to stop collecting the analyte in GC 603. GC 603 and detector 605 can then be operated as described above with reference to the system illustrated in FIGS. 8a–8c.

If it is desired to analyze only semi-volatile organics, such as PCB, PAH, and the like, the more volatile organics, e.g., benzene, carbon tetrachloride, methanol, and acetone, are removed first by heating chamber 653 to a temperature less than the selected desorption temperature, e.g., approximately 100 to 150° C., while valve assembly 607 is still in the flush mode. After venting the volatile organics, valve assembly 607 is switched to run mode and chamber 653 is ballistically heated to approximately 325° C., during which time all organics are sublimated from the wall of chamber 653. The procedure then continues as described above. In this manner, more volatile compounds are removed prior to analyzing less volatile constituents. The less volatile constituents can be detected in isolation from the volatile organics. If it is desired to analyze one or more of the volatiles, chamber 653 can be flushed at a lower flushing temperature, then valve assembly 607 can be put into the run mode while the chamber is ballistically heated to a selected desorption temperature, such as 100 to 150° C. In this manner, the semi-volatiles do not desorb as much as they would at higher temperatures.

When analyzing an organic mixture, which may include an organic constituent in a solvent, the liquid mixture is injected into chamber 653 with a syringe with end cap 625 removed. The volume of the mixture that can be examined depends on the anticipated concentration of the constituent, and may vary from about 1 to 1000 $\mu$L. The horizontal position of thermal desorber unit 601 allows larger amounts of liquid sample to be injected without clogging gas outlet 627 or losing the sample from desorption tube 653. Valve assembly is placed in flush mode while introducing the sample to maintain a flow of carrier gas through GC column and inhibit any oxygen from entering.

After introducing the sample, end cap 625 is sealed, isolating the system from the atmosphere. Valve assembly 607 is maintained in flush mode so as to flow the carrier (or purge) gas through chamber 653 for removing the solvent to exhaust 635. The temperature may be elevated above room temperature to speed the flushing.

After venting the solvent and any oxygen in mixture, valve assembly 607 is placed in run mode and thermal desorber unit 601, including chamber 653, is ballistically heated and the procedure continues as described above in the gas sample example. As in the example for hot gas analysis described above, the organics sublimate off the wall of chamber 653 and are carried with the carrier gas through valve 609 to GC column 603.

The system can also be used to analyze a solid sample, such as, for example, soil, fibers, hair, suspected drugs, arson evidence, or the like, or to analyze a sample bound to an adsorbent material, e.g., TENAX®, or activated charcoal. With valve assembly 607 in flush mode, the sample 689 (see FIGS. 8e and 8f) is placed inside desorption tube 653 while outside of body 651. Desorption tube 653 is then placed in body 651, end cap 655 is put back, and sealed. The procedure then continues as described above for the liquid sample.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A sample analysis system comprising:
   a sample analysis instrument;
   a thermal desorption unit including a body providing a desorption chamber, a removable end cap for closing the chamber, a desorber heating system arranged to heat the desorption chamber from ambient temperature to a desorption temperature by directly heating the body, a gas inlet to the desorption chamber, and a gas outlet from the desorption chamber;
   a valve assembly structured and arranged to operate in a run mode wherein the valve assembly directs a flow of carrier gas to the thermal desorption unit gas inlet, and couples the thermal desorption unit gas outlet to an inlet of the sample analysis instrument, and also structured and arranged to operate in a flush mode wherein the valve assembly directs the flow of carrier gas to the inlet of the gas analysis instrument, directs a flow of flushing gas to the thermal desorption unit gas inlet, and couples the thermal desorption unit gas outlet to an exhaust.

2. The sample analysis system of claim 1, wherein the desorber heating system comprises a circuit arranged to pass a current through the body to heat the body.

3. The sample analysis system of claim 1, wherein the thermal desorption unit further includes a cooling assembly structured and arranged to cool the chamber to a temperature that is below ambient temperature.

4. The sample analysis system of claim 3, wherein the cooling assembly of the thermal desorption unit comprises a solid state cooling device.

5. The sample analysis system of claim 3, wherein the body has an inner dimension and an outer dimension providing a wall thickness of about 1.35 mm or less.

6. The sample analysis system of claim 5, wherein the body is substantially cylindrical and comprises an electrically resistive material.

7. The sample analysis system of claim 5, wherein the body comprises an end wall coated with gold.

8. The sample analysis system of claim 1, wherein the sample analysis instrument comprises a gas phase separation device.

9. The sample analysis system of claim 1, wherein the desorption chamber comprises a tube aligned approximately horizontally.

10. The sample analysis system of claim 1, wherein the thermal desorption unit is structured and arranged to introduce a sample into the desorption chamber without opening the desorption chamber to atmosphere.

11. The sample analysis system of claim 1, wherein the valve assembly includes a valve heating system adapted to heat the valve assembly from ambient temperature to at least 300 degrees Celsius.

12. The sample analysis system of claim 1, wherein the desorber heating system is structured and arranged to ballistically heat the desorption chamber to a temperature of at least 300 degrees Celsius.

13. A method of isolating a constituent from a sample using the sample analysis system of claim 1, the sample comprising the constituent and a solvent, the method comprising:
   introducing the sample into the desorption chamber;
   flushing the solvent out of the desorption chamber by operating the valve assembly in the flush mode to direct a flushing gas through the desorption chamber to the exhaust, whereby the constituent is adsorbed on a wall within the desorption chamber and the solvent is flushed out the exhaust; and
   desorbing the constituent by operating the valve assembly in the run mode to direct a carrier gas through the desorption chamber and into the analysis instrument, and heating the desorption chamber to a desorbing temperature while the carrier gas is flowing therethrough by heating the body directly, thereby desorbing the constituent from the wall of the desorption chamber and carrying the constituent into the analysis instrument with the carrier gas.

14. The method of claim 13, wherein the desorption chamber is heated by passing an electric current through the body of the desorption chamber.

15. The method of claim 13, wherein flushing further includes heating the desorption chamber to a flushing temperature that is lower than the desorbing temperature to flush out sample material being more volatile than the constituent.

16. The method of claim 13, wherein flushing further includes heating the valve assembly while flowing the flushing gas through the desorption chamber.

17. The method of claim 13, wherein desorbing further includes heating the valve assembly while operating in the run mode.

18. The method of claim 13, further comprising cooling the desorption chamber with a solid state cooling device.

19. A method of isolating a constituent from a gas sample that includes volatiles using the sample analysis system of claim 1, the method comprising:
   cooling the desorption chamber to a condensing temperature below ambient temperature while operating the valve assembly in the flush mode to direct a flushing gas through the desorption chamber to exhaust;
   collecting the sample into the cooled desorption chamber while continuing to flush the chamber with flushing gas, thereby adsorbing the constituent onto a wall within the chamber;
   stopping sample collection; and
   desorbing the constituent by operating the valve assembly in the run mode to direct a carrier gas through the desorption chamber and into the analysis instrument, and heating the desorption chamber to a desorbing temperature that is above ambient temperature while the carrier gas is flowing therethrough by heating the body directly, thereby desorbing the constituent from the wall within the desorption chamber and carrying the constituent into the sample analysis instrument with the carrier gas.

20. The method of claim 19, wherein the desorption chamber is heated by passing an electric current through the body of the desorption chamber.

21. The method of claim 19, further comprising flushing volatiles in the sample after adsorbing and before desorbing the constituent, wherein the volatiles are flushed by heating the desorption chamber while in the flush mode to a flushing temperature that is lower than the desorbing temperature.

22. The method of claim 19, wherein the sample is collected while inhibiting oxygen from reaching the sample analysis instrument.

23. The method of claim 19, wherein heating the desorption chamber to the desorption temperature includes heating the desorption chamber from ambient temperature to a temperature of about 320° C. in about 45 seconds or less.

24. The method of claim 19, wherein desorbing further includes carrying the desorbed constituent into a gas phase separator, and separating the constituent from other sample components desorbed from the chamber in the separator.

25. The method of claim 19, wherein cooling the desorption chamber includes cooling the body with a solid state cooling device.

26. A method of isolating a constituent from a solid sample using the sample analysis system of claim 1, the method comprising:

placing the solid sample within the desorption chamber while the valve assembly is in the flush mode;

sealing the desorption chamber from atmospheric air while continuing to operate in the flush mode; and desorbing the constituent by operating the valve assembly in the run mode to direct a carrier gas through the desorption chamber, and heating the desorption chamber to a desorbing temperature while the carrier gas is flowing therethrough, thereby desorbing the constituent from the solid sample and carrying the constituent to the inlet of the sample analysis instrument with the carrier gas.

27. The method of claim 26, wherein the desorption chamber is heated by passing an electric current through the body of the desorption chamber.

28. The method of claim 26, wherein the desorption chamber is heated to the desorption temperature from ambient temperature within 6 to 12 seconds or less.

29. The method of claim 26, wherein desorbing further includes carrying the desorbed constituent into a gas phase separator, and separating the constituent from other sample components desorbed from the chamber in the separator.

30. The sample analysis system of claim 1, wherein heating the body directly includes heating the desorption chamber ballistically.

31. The sample analysis system of claim 30, wherein heating the desorption chamber ballistically includes heating from ambient temperature to about 320° in 45 seconds or less.

32. The sample analysis system of claim 30, wherein heating the desorption chamber ballistically includes heating the desorption chamber at a rate of at least about 20° C. per second.

33. A sample analysis system, comprising:

a sample analysis instrument;

a thermal desorption unit including a body providing a desorption chamber, a removable end cap for closing the chamber, a desorber heating system arranged to heat the desorption chamber, a gas inlet to the desorption chamber, and a gas outlet from the desorption chamber;

a valve assembly structured and arranged to operate in a run mode wherein the valve assembly directs a flow of carrier gas to the thermal desorption unit gas inlet, and couples the thermal desorption unit gas outlet to an inlet of the sample analysis instrument, and also structured and arranged to operate in a flush mode wherein the valve assembly directs the flow of carrier gas to the inlet of the gas analysis instrument, directs a flow of flushing gas to the thermal desorption unit gas inlet, and couples the thermal desorption unit gas outlet to an exhaust, wherein the valve assembly includes a multi-port valve, a first port being coupled to a carrier gas supply, a second port being coupled to the thermal desorption unit gas inlet, a third port being coupled to the thermal desorption unit gas outlet, a fourth port being coupled to the sample analyzer gas inlet, a fifth port being coupled to a purge gas supply, and a sixth port being coupled to the exhaust.

34. The sample analysis system of claim 33, wherein the valve assembly further includes a flow controller comprising a flow controller inlet coupled to the carrier gas supply, a first flow controller outlet coupled to the first port, and a second flow controller outlet connected to the fifth port, the flow controller being structured and arranged to selectively couple the flow controller inlet to any of the first flow controller outlet, the second flow controller outlet, and both the first and second flow controller outlets, wherein the carrier gas supply also serves to flush the desorption chamber in the flush mode.

35. A sample analysis system comprising:

a sample analysis instrument;

a thermal desorption unit including a body providing a desorption chamber, a removable end cap for closing the chamber, a desorber heating system arranged to heat the desorption chamber, a gas inlet to the desorption chamber, and a gas outlet from the desorption chamber, wherein the end cap is structured and arranged to introduce a sample into the desorption chamber without opening the desorption chamber to atmosphere;

a valve assembly structured and arranged to operate in a run mode wherein the valve assembly directs a flow of carrier gas to the thermal desorption unit gas inlet, and couples the thermal desorption unit gas outlet to an inlet of the sample analysis instrument, and also being structured and arranged to operate in a flush mode wherein the valve assembly directs the flow of carrier gas to the inlet of the gas analysis instrument, directs a flow of flushing gas to the thermal desorption unit gas inlet, and couples the thermal desorption unit gas outlet to an exhaust.

* * * * *